United States Patent
Stacey et al.

(10) Patent No.: US 11,429,911 B2
(45) Date of Patent: Aug. 30, 2022

(54) SCALING TOOL

(71) Applicant: The Automation Partnership (Cambridge) Limited, Royston (GB)

(72) Inventors: Adrian Stacey, Cambridge (GB); Jochen Scholz, Göttingen (DE)

(73) Assignee: The Automation Partnership (Cambridge) Limited, Royston (GB)

( * ) Notice: Subject to any disclaimer, the term of this patent is extended or adjusted under 35 U.S.C. 154(b) by 69 days.

(21) Appl. No.: 16/962,550

(22) PCT Filed: Jan. 31, 2019

(86) PCT No.: PCT/EP2019/052312
§ 371 (c)(1),
(2) Date: Jul. 16, 2020

(87) PCT Pub. No.: WO2019/154700
PCT Pub. Date: Aug. 15, 2019

(65) Prior Publication Data
US 2020/0349487 A1    Nov. 5, 2020

(30) Foreign Application Priority Data

Feb. 12, 2018   (EP) .................................. 18000132

(51) Int. Cl.
*G06Q 10/06* (2012.01)
*G05B 19/418* (2006.01)
(Continued)

(52) U.S. Cl.
CPC ......... *G06Q 10/06313* (2013.01); *C12Q 3/00* (2013.01); *G05B 19/41885* (2013.01);
(Continued)

(58) Field of Classification Search
None
See application file for complete search history.

(56) References Cited

U.S. PATENT DOCUMENTS

| 8,160,735 | B2 | 4/2012 | Sinclair et al. |
| 9,069,345 | B2 | 6/2015 | McCready et al. |

FOREIGN PATENT DOCUMENTS

| KR | 10-2011-0110341 | 10/2011 |
| WO | WO01/80055 | 10/2001 |

(Continued)

OTHER PUBLICATIONS

International Search Report and Written Opinion for PCT/EP2019/052312, dated Apr. 3, 2019.
(Continued)

*Primary Examiner* — Sean Shechtman
(74) *Attorney, Agent, or Firm* — Klarquist Sparkman, LLP

(57) ABSTRACT

The present application generally pertains to scaling of a production process to produce a chemical, pharmaceutical and/or biotechnological product and/or of a production state of a respective production equipment. Particularly, there is provided a computer-implemented method of scaling a production process to produce a chemical, pharmaceutical and/or biotechnological product, the scaling being from a source scale to a target scale, wherein the production process is defined by a plurality of steps specified by one or more process parameters controlling an execution of the production process, the method comprising: (a) retrieving: parameter evolution information that describes the time evolution of the process parameter(s); a plurality of recipe templates, wherein a recipe comprises the plurality of steps defining the production process, and wherein a recipe template is a recipe in which at least one of the process parameters specifying the plurality of steps is a parameter being variable and having no predetermined value at the outset; (b) receiving: a source setup specification of a source setup to be used for
(Continued)

executing the production process at the source scale, the source setup specification comprising the source scale value: a target setup specification of a target setup to be used for executing the production process at the target scale, the target setup specification comprising the target scale value; a source recipe defining the production process at the source scale: at least one acceptability function defining conditions for the values of the process parameter(s) at the source scale and/or at the target scale; (c) simulating the execution of the production process at the source scale using the source setup specification, the source recipe and the parameter evolution information: (d) determining, from the simulation, one or more source trajectories for the process parameters), wherein a trajectory corresponds to a time-based profile of values recordable during the simulated execution of the production process; (e) performing a target determination step comprising: selecting a recipe template pertinent to the production process out of the plurality of recipe templates; providing an input value for the at least one variable parameter in the selected recipe template; simulating the execution of the production process at the target scale using the target setup specification, the selected recipe template, the input value for the at least one variable parameter and the parameter evolution information; determining, from the simulation, one or more target trajectories for the process parameters; comparing the source trajectory(ies) and the target trajectory(ies); computing, based on the comparison and on the at least one acceptability function, an acceptability score for the selected recipe template; computing an optimal value for the at least one variable parameter in the selected recipe template by optimising the acceptability score and/or computing an acceptable range for the at least one variable parameter, wherein values within the acceptable range yield an acceptability score above a specific threshold; (f) if there is at least another pertinent recipe template, repeating the target determination step for at least another pertinent recipe template; (g) selecting at least one of the plurality of recipe templates and corresponding computed value(s) for variable parameters) as target recipe based on the acceptability scores computed for one or more recipe templates.

11 Claims, 9 Drawing Sheets

(51) Int. Cl.
  *G06Q 50/04* (2012.01)
  *C12Q 3/00* (2006.01)
(52) U.S. Cl.
  CPC ... *G06Q 50/04* (2013.01); *G05B 2219/32287* (2013.01); *G05B 2219/32301* (2013.01)

(56) References Cited

FOREIGN PATENT DOCUMENTS

WO  WO2007/017738  2/2007
WO  WO2017/199006  11/2017

OTHER PUBLICATIONS

Decision to Grant a Patent (including an English translation) issued by the Korean Intellectual Property Office dated Mar. 30, 2022, for Korean Patent Application No. 10-2020-7022590, 14 pp.

Examination Report under Sections 12 & 13 of the Patents Act, 1970 and the Patents Rules, 2003 (in Hindi and including English translation within) issued by Intellectual Property India dated Apr. 22, 2022, for India Patent Application No. 202037034698, 6 pp.

SCALING TOOL

CROSS REFERENCE TO RELATED APPLICATIONS

This is the U.S. National Stage of International Application No. PCT/EP2019/052312, filed Jan. 31, 2019, which was published in English under POT Article 21(2), which in turn claims the benefit of European Application No. 18000132.3, filed Feb. 12, 2018, which applications are incorporated herein in their entireties.

TECHNICAL FIELD

The following description relates to processes for the production of chemical, pharmaceutical and/or biotechnological products. In particular, aspects of the application relate to scaling a process across two or more scales.

BACKGROUND

Processes for the production of chemical, pharmaceutical and/or biotechnological products are scale dependent; in other words, a process behaves at least partly differently on a small scale (e.g., in a laboratory) in comparison to a large scale (e.g., in production). Usually the process is first performed at small scales and then at successively larger scales.

However, at each scale transition, there is a risk that process performance will be lost. This loss could be a catastrophic failure at the larger scale, or simply a reduction in product quality or titre. The problem of process performance arises because it is not possible to keep all process and physical parameters constant across the scales. For example, mixing time, which is an important driver in terms of the microenvironment seen by cells in a bioreactor, tends to increase with scale. To compensate for this, larger stirrer speeds could be selected at the larger scales. However, this would dramatically increase the specific power input, which in itself may be detrimental to the cells or product. Similarly, at the smaller scales, evaporation and sampling comprise a larger proportion of the bioreactor volume than at the larger scale.

Thus, there is a problem relating to how to best scale up a process that has been found to be optimal at the small scale, or, in other words, how to best translate a process from a source scale to a target scale, possibly passing through intermediate target scales.

In current approaches to translation between scales a scale-independent parameter is used as an intermediary or link between different scales. Starting from a set of known parameters for the source setup configuration (such as stir speed, fill volume and gassing rate for a bioreactor), a scale-independent parameter (e.g. power input per volume) is derived by combining the known parameters. Then a given parameter is set for the target setup configuration (e.g. a desired fill volume). Finally, the remaining parameters for the target setup configuration (e.g. stir speed and gassing rate) are calculated to match the previously obtained value for the scale-independent parameter.

However, the above-illustrated approach for scale conversion is affected by several issues:

- It uses only a single scale-independent variable as intermediary between the scales, whereas these processes require a careful compromise between a plurality of variables.
- It deals with scale translations as if they were only single-step translations, i.e. from one source scale directly to a single target scale, whereas often scale translation occurs across multiple scales (a so-called "scaling train"). In other words, in typical approaches, each translation considers only two scales at a time, without considering possible subsequent translations. Thus, subsequent transitions (e.g. to even larger scales) may then be problematic if the first transition leads to a "dead end" because no account was taken of the end goal. A "dead end" is a configuration from which subsequent scaling is risky in terms of the prospect of failed translation. For example, translation from a small to an intermediate scale might favour a very low stir speed at the intermediate scale (for example, to maintain low shear in the cell environment), but such low stir speed may then not be translatable to the large scale because of the consequences for mixing time.
- It fails to take into account the fact that the consequences of a difference in variables between scales may not be symmetric. For example, mixing time considerations are highly asymmetric: decreasing mixing time is not normally an issue, but increasing mixing time is likely to be. Similarly, a process might be immune to an increase in $k_La$ but not to a decrease in it.
- It does not provide a means by which prior information about what constitutes an optimum process (e.g. a desire to reduce energy input at large scales, a desire to sample frequently at small scales) can be integrated with the need to match certain conditions between scales. This prior information includes two aspects. First, goals in terms of constraints in how it is desirable to run the bioreactors. For example, a user may want to run the bioreactors with particular constraints e.g. between 5% and 95% maximum stir speed. Second, knowledge about the sensitivities of the organism or the process e.g. a particular organism or process may be highly oxygen demanding, highly pH sensitive etc. and translation needs to take this into account. Similarly, a particular organism, product or process may be shear sensitive and therefore this needs to be taken into account in terms of tip speed/eddy size/etc when translating. In typical approaches, prior process knowledge is not taken into account when scaling. It is rather introduced post hoc, resulting in unrealistic process parameter values.
- It provides a binary outcome regarding one or more parameters at the target scale, i.e. either good/acceptable or bad/unacceptable. In reality there is a range of possible values to which a lower or higher risk of deteriorating the process performance is associated. In other words, the prior art approach does not provide means to investigate sensitivity of the process to one or more parameters
- It does not provide a means of scaling processes from one scale to another by taking into account the process as a whole, focussing instead on single timepoints within a process. Optimisation of certain timepoints within a process may be detrimental for other timepoints, if the process is not considered in its entirety.

Accordingly, there is a need for a scaling approach that reduces the risks associated with scale transitions. In particular, there is a need for identification of appropriate process conditions at large scale to reduce risks related to poor process performance at successively larger scales.

SUMMARY

It is an object of the invention to transfer a process (for the production of a chemical, pharmaceutical and/or biotechnological product) from a source scale to a target scale in a manner that maximises the similarity of the process between the scales in terms of successfulness of the process. The process is similar at different scales if important predictors of performance (for example in terms of productivity or titre) as determined from prior knowledge are themselves similar between source process and target process.

For example, if a process at a source scale resulted in a low percentage of dissolved oxygen (DO) throughout the process, a good translation at the target scale would typically maintain a low percentage of DO throughout the process, for example by adjusting stir speed or gassing. The percentage of DO is known to be usually a predictor of the performance of the organism and also of productivity and quality. Even if a higher DO percentage may, in some cases, be better in terms of productivity or quality at the target scale, a scaling leading to higher DO percentage would not be considered good because the similarity between the processes is lower. However, if the organism is known to be insensitive to the DO percentage, the similarity between process will be evaluated based on other aspects that actually influence the product.

In particular, the scaling should not just optimize the outcome of the process at the target scale, e.g. quality and yield of the product. Rather, also the process itself is optimised in terms of similarity between different scales. Accordingly, the best match between the process at the source scale and the process at the target scale is found both from the perspective of the process itself and of the product.

In other words, it is an object of the invention to identify how to run a process at a given scale (e.g. a larger scale) to maximise the chance of obtaining the same performance obtained at another scale (e.g. a smaller scale). It is also an object of the invention to identify how to run a process at a given scale (e.g. a smaller scale) given anticipated deployment at another scale (e.g. a larger scale). Particularly, it is envisaged identifying the range of process variants that can be run at the smaller scale with a reasonable expectation of them performing similarly at a larger scale or scales. Thus, when a process is optimised (by experimentation, within a determined range) at small scale, the optimised process then translates back well to larger scale.

It is another object of the invention to identify potential issues with a process in silico prior to deployment on hardware, and to find process alternatives which overcome these issues.

The achievement of these objects in accordance with the invention is set out in the independent claims. Further developments of the invention are the subject matter of the dependent claims.

According to one aspect, a computer-implemented method of scaling a production process to produce a chemical, pharmaceutical and/or biotechnological product is provided.

Examples of processes according to the present application are industrial processes, particularly biopharmaceutical processes. Other examples include research and development processes or scientific research.

Examples of inputs or ingredients for a production process according to the present application may include biological material, i.e. materials comprising a biological system, such as cells, cell components, cell products, and other molecules, as well as materials derived from a biological system, such as proteins, antibodies and growth factors. Further ingredients may include chemical compounds and various substrates.

Examples of inputs may include gasses and liquids. Gasses are any or all of air, oxygen, nitrogen, oxygen-enriched air and carbon dioxide. Liquids are typically:
    media (nutrient mix in buffer e.g. glucose+amino acids+ salts+water)
    inoculum (organism at relatively high density in media)
    base (used to modulate pH e.g. ammonium hydroxide solution)
    acid (used to modulate pH e.g. HCl solution)
    nutrient feed (high concentration nutrient mix in buffer)
    inducer (modulates behaviour of organism).

A production process of the present application may involve chemical or microbiological conversion of material in conjunction with the transfer of mass, heat, and momentum. The process may include homogeneous or heterogeneous chemical and/or biochemical reactions. The process may comprise but is not limited to mixing, filtration, purification, centrifugation and/or cell cultivation. The production process may involve chemical or biological reactions that take time to complete, e.g. 6 hours for an *E. coli* microbial batch and 60 days for a mammalian perfusion process.

In particular, "producing" a chemical, pharmaceutical and/or biotechnological product indicates any processing of the inputs, including but not limited to modifying a state of any of the inputs (e.g. changing the temperature, oxygen content etc. thereof), combining any of the inputs reversibly or irreversibly, using the inputs for creating new material.

Possible products may include a transformed substrate, baker's yeast, lactic acid culture, lipase, invertase, rennet. Further exemplary biopharmaceutical products that can be produced according to the techniques described in the present application include the following; recombinant and non-recombinant proteins, vaccines, gene vectors, DNA, RNA, antibiotics, secondary metabolites, growth factors, cells for cell therapy or regenerative medicine, half-synthesized products (e.g. artificial organs). Various production systems may be used to facilitate the process, e.g. cell based systems such as animal cells (e.g. CHO, HEK, PerC6, VERO, MDCK), insect cells (e.g. SF9, SF21), microorganisms (e.g. *E. coli, S. ceravisae, P. pastoris*, etc.), algae, plant cells, cell free expression systems (cell extracts, recombinant ribosomal systems, etc.), primary cells, stem cells, native and gene manipulated patient specific cells, matrix based cell systems.

Exemplarily, the production process may be a batch process, in which a specific amount of feed medium for feeding an organism is provide as an initial condition and then a control period follows.

The production process may be a fed batch process. The fed batch process may involve a culture in which a base medium supports initial cell culture and a feed medium is added to support further growth or product production, once the initial nutrients have been depleted. In other words, the fed batch process may involve a batch period followed by a feed period.

The production process may be a perfusion process, in which a batch period is followed by a feed period with continual removal of the product, e.g. by filtration.

Techniques described in the present application may be useful for bioreactor processes, and for processes carried out at other levels of production.

The production process is defined by a plurality of steps specified by one or more process parameters controlling an execution of the production process.

The production process is defined by the sequence of steps that is performed in order to arrive at the product.

Some steps may occur simultaneously to one another and other steps may occur in a temporal sequence after one another. A step may correspond to an action carried out during the production process, wherein the action may be passive, such as waiting for an event to occur (such as an increase in oxygen levels due to inactivity of the culture), or active, such as causing an event to occur (e.g. stirring or adding a fluid) or setting values and/or profiles for a given quantity.

Exemplarily, steps that perform actions within a production process in a bioreactor may be typified by the following non-exhaustive list:
- set a set point in terms of stirring, gas supply, gas mix, temperature
- perform a profiled change in terms of stirring, gas supply, gas mix, temperature
- add a selected liquid to bioreactor vessel
- remove liquid from bioreactor vessel
- specify the connection of particular fluids to the bioreactor and the composition of such fluids.

Further, the process may comprise step types that describe the flow of execution, e.g. specifying how/when an event occurs, such as: repeat a step or steps until a condition is met and/or for a specified number of iterations, choose between various options depending on state of bioreactor, wait until a condition becomes true (e.g. wait until dissolved oxygen rises to indicate end of batch phase before starting feed), perform a step or set of steps concurrently (e.g. perform pH control at the same time as temperature control).

The execution of the plurality of steps is controlled by one or more process parameters. Exemplarily, the plurality of steps may be specified by a plurality of parameters, with each step being defined by one or more process parameters.

In other words, the production process may include (i.e. may be performed according to) at least one process parameter that has an influence on performance of the process (e.g., product titer, quality attributes) and the product produced by the process.

The process parameters control the execution of the process in the sense that they influence the course of the process, but at least some of them may also be in turn influenced by the process. Further, process parameters may influence each other.

Specifically, some of the process parameters may be controllable, i.e. the values of at least some of the process parameters may be specifically adjusted prior to and/or during performing the process. In other words, at least one of the process parameters can be set e.g. by an operator or by a control system. In particular, these parameters may be the ones describing and/or governing a state and/or behaviour of the equipment used for the production process, e.g. a bioreactor. In the following, these parameters may also be referred to as "recipe parameters", because they can be set in recipes, as explained below.

Accordingly, the adjustable process parameters may be a proper subset of process parameters. In the case of a bioreactor these may include but are not limited to:
- one or more parameters related directly to interventions in the bioreactor, e.g. amount of liquid to remove in a sampling step;
- one or more parameters providing an input to a control loop, e.g. the set point for oxygen in the bioreactor (a control loop in the bioreactor system would then monitor oxygen and adjust e.g. stirring or gassing to hit the set-point);
- one or more parameters providing an input to a profile e.g. the rate exponent in exponential increase of feed; and/or
- one or more parameters specifying a condition to be met (e.g. dissolved oxygen must reach 90% before fed phase can start).

Exemplarily, the recipe parameters for a bioreactor may be or include stir speed, temperature, gassing, liquid addition, sampling, relative profiles and indications about which liquids to add.

In particular, the adjustable parameters may be given a constant, fixed value expressed by a given number or a value expressed as a function of an argument, wherein the argument may be another process parameter (having a constant value or a changing value) or another quantity, such as time. Accordingly, the values for the adjustable parameters may be set at the outset of the execution of the production process or may be dynamically determined during the execution of the production process. For example, set points and profiles may be dynamically determined to take into account events arising during the production process.

The process parameters may further include one or more parameters describing the state of the production, which is of course at least partly determined by the behaviour of the equipment, as well as by the specifics of the equipment and the inputs (e.g. organism) used. The values of these parameters may be intrinsic to the production process and not directly adjustable. However, they may be indirectly adjustable by modifying factors that affect them, such as the recipe parameters.

The values of these parameters may change during the production process and, thus, in the following they may be referred to as "dynamic parameters". The measured value of a dynamic parameter at a given time during the process (either executed in the real world or simulated) corresponds to what is usually referred to as "process value" or "process variable".

For example, the dynamic parameters for a production process in a bioreactor may be classified as:
a. calculable knock-on effects of the recipe parameters as a result of the geometry and capabilities of the bioreactor, e.g. tip speed, stir speed as proportion of maximum bioreactor stir speed, superficial gas velocity;
b. knock-on effects that can be obtained from previous empirical research e.g. $k_L a$, mixing time, power input, minimum eddy size;
c. variables that can be calculated from those in point (b) together with properties of the bioreactor e.g. power per unit volume;
d. variables which, due to a control loop in the process, arise from feedback from simulated bioreactor properties and aspects of the process, e.g. gassing rate, gas mix and stir speed;
e. variables that result from the dynamics of oxygen or other gasses within the bioreactor as affected by e.g. stir speed, gassing etc., e.g. DO, partial pressure of carbon dioxide (ppCO2);
f. variables that result from the dynamics of the organism, as dictated by an organism model and the other variables above and below (e.g. cell count, cell activity, cell metabolism);
g. variables that result from liquid addition or removal calculable from the recipe parameters, e.g. fill volume, and potentially a model for evaporation;
h. variables that result from a combination of liquid addition and removal and also the dynamics of the organism, e.g. concentrations of analytes.

Exemplarily, the process parameters comprise both recipe parameters and dynamic parameters.

Based on the above, examples of process parameters may include but are not limited to: temperature (affects cell growth), volume, pH (affects cell growth), specific buffering capacity (affects rate of pH change), cell density, cell activity state (mean), cell metabolic state (mean), $k_L a$ (affects oxygen transfer), Reynolds number (affects mixing time and cell growth), Froude number, mixing time, power input, power input per volume, stir speed, tip speed, tip speed as a proportion of maximum possible tip speed in system, gassing rate, gassing mix, minimum eddy size (potentially affects cell health), superficial gas velocity, concentration of abstracted nutrients e.g. primary carbon source, secondary carbon source, waste products, product, base, acid, primary nitrogen source, secondary nitrogen source, inducer, key analytes e.g. product quality, cell debris, protein concentration (may affect foam production, for example), cell parameters e.g. cell subpopulations, bioreactor heterogeneity e.g. variation in temperature within bioreactor, fluid dynamic properties e.g. proportion of time cells inhabit high shear environments, proportion of bioreactor that is relatively free of stirring (dead zones), proportion of bioreactor swept by impeller per unit time, carbon dioxide and carbonic acid dynamics, antifoam concentration (interacts with $k_L a$ and other gas transfer) and foam accumulation parameters (function of SGV and also protein concentration, for example).

The scaling of the process is performed between a source scale and a target scale.

A scale particularly refers to a configuration, e.g. a size of a setup used for executing the production process, wherein the configuration determines, among others, the throughput and the costs of the production process. Exemplarily, for a production process executed with a bioreactor, the scale value may refer to the volume of the bioreactor and/or to one or more components thereof such as impellers (e.g. type and/or size thereof). A range of scales at which production processes are typically executed includes 2 mL (e.g. in microfluidic examples), less than 15 mL, 15 mL, 250 mL, 2 L, 10 L, 50 L, 200 L, 1000 L and 2000 L. Bioreactors operating at these scales include Sartorius products such as Ambr®, UniVessel® and BIOSTAT STR®. The scales may be divided into three groups: small scale, intermediate scale and large scale. Some scales may belong to more than one group. For example, 2 L could be both small scale and intermediate scale and 50 L could be both intermediate scale and large scale.

Scaling the process indicates that a process designed and/or tested at a source scale is adapted for a target scale so that the process is still successful. The successfulness of the process may be evaluated e.g. on the basis of the amount of product produced (titre), the quality of the product (e.g. chemical composition, including glycosylation, and folding pattern of protein) and the presence/absence of other factors in the media causing difficulty in purification downstream. For example, quality attributes may be used to assess the successfulness, wherein quality attribute may be a physical, chemical, biological or microbiological property that should be within an appropriate limit, range, or distribution to ensure desired product quality.

When scaling the process, one or more of the plurality of steps may be modified, in particular one or more of the process parameters, in particular the recipe parameters, specifying the steps may be changed. Further, in some examples, the plurality of steps may be modified in that one or more steps are added or removed, an action is modified e.g. by adding a dependence on a condition and/or the order of the steps is changed.

The reasons for which production processes are performed at a given scale and then scaled are the following. Executing a production process at large scales is expensive, e.g. more than 10000 Euros per run. Many variables contribute to success of production and these are not a priori known for each process. Therefore small scale experiments are performed to identify a producing organism (clone) and to optimise the production process prior to transfer to large scale. A typical workflow according to which a production process is implemented is as follows:

very small scale (e.g. 15 mL or less): identification of clone in representative process with a large number of trials (e.g. 48 to 1000);

small scale (e.g. 250 mL or 2 L): refinement of process with an intermediate number of trials (e.g. 24 to 96) with the purpose of modifying the process until success factors are maximised;

intermediate scale (e.g. 50 L): initial process transfer, potential further process refinement;

manufacture scale (e.g. 1000 L): repeated production of product.

At each stage, there is a degree of optimisation such as selection of clones based on best performing clones or selection of best gassing conditions. In each stage transition, not all parameters can be matched between scales because the translation is non-linear. In particular:

demands at each stage may be different e.g. the amount of sample required is small at small scale (few tests) and larger (e.g. >1 mL) later, but actually smaller relative to total bioreactor size or minimising energy input is not an issue at small scale, may be an issue at larger;

opportunities may be different, in that it is cheaper to do a large number of runs at small scale and also automated variation of process parameters is relatively easy at small scale;

constraints may be different: accuracy of pH control/gassing is potentially lower at smaller scale, the availability of analytics increases with scales, the tolerance to intervention (e.g. sampling) decreases towards manufacturing scale, aspects of bioreactors at given scale change what can be achieved (e.g. at larger scale, it is increasingly difficult to remove adequate heat from microbial culture and/or mixing time tends to increase).

In light of the above issues, there is a need to make small scales as representative as possible of large scales, make each stage in process translation as low risk as possible (i.e. minimise the risk of change of success criteria) also taking into account the risk for subsequent steps.

In some examples, the source scale may be smaller than the target scale, e.g. the source scale may be 250 mL and the target scale may be 2 L. In other examples, the source scale may be the same as the target scale, but there may be different constraints on the production process, e.g. a shorter process time may be desired. Alternatively, the scales may be the same but the configuration of the equipment may be different, e.g. a BIOSTAT STR® 50 with a 3-blade impeller and a 6-blade impeller and a BIOSTAT STR® 50 with two 3-blade impellers. In such cases, one of the objectives of the scaling may be to maximise the chance of obtaining at the larger scale the same performance obtained at the smaller scale.

In yet other examples, the source scale may be larger than the target scale. This may be the case if some operations for optimising the process can be done more quickly and at lower costs at a smaller scale. Thus, starting from an actually executed process at a larger scale, the objective of the scaling may be determining a range of process variants (in terms of steps and/or parameters) that can be run at the smaller scale and then scaled back to the original larger scale with a good performance. For example, the scaled down process could be used to select between different clones, i.e. the aim is to find the clones that will perform will when scaled up. Indeed, several clones can be tested at small scales (e.g. in the order of thousands at the <15 mL scale, or about 50 at the 15 mL scale).

The method comprises retrieving parameter evolution information that describes the time evolution of the process parameter(s).

The parameter evolution information characterises how the one or more process parameters change with time, including initial conditions for the process parameters. In particular, the parameter evolution information may comprise relations empirically derived from previous executions of the production process and/or equations derived by theoretical model about the evolution of the production process. The evolution information may comprise the explicit dependence of one or more parameters on time together with relations linking the process parameters to each other. The parameter evolution information may also comprise information about variables that do not directly specify the steps of the production process, but that indirectly affect the process parameters and, hence, the execution of the production process.

Parameter evolution information may have a number of constituent parts e.g. parameter evolution information related to cell dynamics, to bioreactor dynamics and/or to chemical reactions occurring within the bioreactor.

For example, the parameter evolution information may comprise empirically derived mappings between recipe parameters (such as stirring speed, gassing rate and fill volume) and dynamic parameters (such as mixing time, $k_L a$ and power input). Additionally or alternatively, the parameter evolution information may comprise theoretically-derived or empirically derived equations and starting points for a cell culture model.

The parameter evolution information may also describe events related and going beyond what may be strictly considered to be the production process per se. In particular, the parameter evolution information may also describe what happens outside a bioreactor e.g. time evolution of samples taken, or in a secondary reactor vessel, or in a downstream processing facility (e.g. a purification unit), and/or in a piece of analytics equipment.

In one example, the cell culture is modelled using a hierarchical set of ordinary differential equations describing "cell processes", where any individual cell process describes, amongst other things, the dependencies of that cell process, i.e. how its rate depends on pH, DO, temperature, and concentrations of various nutrients, and the results of that process, i.e. the change that occurs in cell count, titre, pH, DO etc. as a result of that process being active.

A given cell process A is allowed to depend on one or more driving processes, X, Y . . . such that the rate of A is computed and then multiplied by either the sum or product of the rates of X, Y. A given cell process may depend on no driving cell process or any number of driving cell processes, and a given cell process may drive no other cell process or any number of other cell processes.

In a very simple case, for example, where there is just one dependency (on temperature) and one consequence (cell growth), this amounts to solving the differential equation:

$$\frac{d\rho}{dt} = \frac{r_g N(T - T_{opt}, T_{sens})}{\rho}$$

where $\rho$ is cell density, t time, $r_g$ maximum growth rate, T temperature, $T_{opt}$ optimum growth temperature, $T_{sens}$ indicates the sensitivity of the growth to the temperature, and N(x,s) denotes the value of a normal distribution with standard deviation s at x.

A more typical case would have considerably more dependencies (e.g. dependency on key nutrients) and consequences (e.g. reduction in DO due to cell activity, elevation of temperature in the case of microbial cell activity, reduction in quantities of nutrients etc). In addition, there may be a number of such cell processes with an additive effect e.g. constitutive growth, death due to toxin presence, product accumulation, etc.

The parameter evolution information for the cell growth then amounts to describing the "cell processes" parameters and dependencies on each other. This may take several forms:

a. Tabulated data (such as could be present in a spreadsheet) whereby each of the cell processes has a row to itself, and within each row, the parameters for the various potential dependencies are supplied (with respect to a hard-coded library of functional forms for the dependencies)

b. Database tables, for example, where there may be tables for

DB_CELL_CULTURE_MODEL,
DB_CELL_CULTURE_PROCESS,
DB_CELL_CULTURE_PROCESS_LINK,
DB_CELL_CULTURE_PROCESS_DEPENDENCY,
DB_CELL_CULTURE_PROCESS_DEPENDENCY_PARAMETER, where DB_CELL_CULTURE_MODEL catalogues the named models which can then be referenced by the software, DB_CELL_CULTURE_PROCESS catalogues the cell culture processes within any model, DB_CELL_CULTURE_PROCESS_LINK relates entries in DB_CELL_CULTURE_PROCESS together to indicate the fact that some processes drive others, DB_CELL_CULTURE_PROCESS_DEPENDENCY indicates particular dependencies (e.g. by indicating the trajectory variable of the dependency and the form of the dependency), and so on.

c. Structured data formats such as XML, or equally JSON or a proprietary form.

These data might then be stored in several ways:

a. Within the software responsible for performing scale conversion, for example, embedded within a DLL or executable b. In files available to the s/w on a file system (a file might supply any of these forms)

c. Within a database instance

The data might further then be stored and accessed:

a. Locally to the software performing the conversion e.g. on the same file system, or accessed by a database engine built into the s/w, potentially within memory, SD card, hard drive, CDROM, DVDROM etc.

b. Within a file share on a network accessible to the software c. Across a client/server (e.g. webservice) system, with the client physically separated from the server, that is, located close to the software (physically), or accessible across a network by the software, in the latter case either stored in one location or distributed across multiple sites.

In addition to the cell culture, physical dynamics of the process are described in the parameter evolution information. This comprises how parameters are related to each other at a point in time and how each parameter evolves over time.

As with the cell culture model, the model for physical dynamics may be stored as XML, database tables, and so on and the substrate for the data could be DVD, CDROM, hard disk etc., and the location of the data local or distinct, and the distribution of the data in one place or distributed.

To summarize, the data representing the parameter evolution information may be retrieved according to a plurality of different implementations. In particular, the data may be already stored as such prior to retrieving or they may be computed on the fly when needed.

The method comprises retrieving a plurality of recipe templates.

A recipe comprises the plurality of steps defining the production process. In other words, a recipe is a structured representation of the production process, e.g. of the activity of a bioreactor. This means that the plurality of steps are expressed in a structured manner, e.g. in a format that can be interpreted by a machine.

As already explained above, there are steps indicating an action (passive or active) and steps controlling the flow, e.g. sequence (execute the contained steps in sequence), repeat (repeat the contained steps until a condition is met or a given number of times) and choice (depending on a condition, perform one step or another).

As discussed, the actual behaviour of the steps during (real or simulated) execution, i.e. what happens is determined by one or more of the process parameters, wherein these include both recipe parameters and dynamic parameters. However, the recipe may comprise only the recipe parameters, i.e. those that can actually be set in order to run the process. The process parameters may be expressed as numbers, as algebraic expressions or as functions of other variables.

Accordingly, the recipe particularly comprises the plurality of steps as well as one or more values for the recipe parameters specifying the steps. In other words, the recipe particularly provides a well-defined procedure that can be directly implemented when executing the production process and that dictates how the process equipment is controlled with time. The values may be dynamically fed to the recipe during execution, but in any case it is predetermined which values will be fed.

Conversely, a recipe template particularly is a recipe in which at least one of the recipe process parameters specifying the plurality of steps is a parameter being variable and having no predetermined value at the outset.

Accordingly, a recipe template involves one or more degrees of freedom on how to execute the production process. Different values for the at least one variable parameter results in different recipes being produced from a given template. The difference may be in the values of the process parameters only or also in the sequence of steps, e.g. if a path within a template is contingent on a variable parameter. Multiple parameters might be free within one recipe template.

Exemplary parameters that would be free to vary (i.e. variable parameters) may include but are not limited to one or more of the following:

Concerning attachments to the bioreactor system
Concentration of primary carbon source in batch media
Concentration of primary nitrogen source in feed media
pH of the acid attached for top control of pH
buffering capacity of the batch media
density of cells in the inoculum
percentage of oxygen in oxygen-enriched air Concerning profiles and set-points
The supply rate for constant gassing in batch phase
The rate at which stir speed is incremented over time in the batch phase
The P or I parameter in a PI feedback loop for gassing control
The maximum air flow rate before oxygen supplementation occurs
The exponential coefficient in an exponential profile for feed
The initial feed rate in an exponential profile for feed
The duration of a plateau phase in a feed profile (for example, after an exponential period)
The rate of temperature drop during a temperature shift for induction
Temperature setpoint during batch phase Concerning discrete events in recipes
Bioreactor fill volume (as a proportion of total bioreactor volume)
Inoculum volume (as a proportion for example, of bioreactor fill volume)

Concerning recipe structure and flow control
The cascade order (e.g. stirring then gassing then O2 supplementation; or gassing then stirring then O2 supplementation) in DO control
Threshold for primary carbon source and/or dissolved oxygen (DO) to initiate fed phase
Frequency of sampling
Volume of sample each time a sample is taken
Threshold primary carbon source in sample to cause feed supplementation
Threshold cell density to initiate harvest.

Different recipe templates may be used at granularity of different organisms, clones, or production processes, deployment systems (e.g. disposable v stainless steel reusable production bioreactors). There may be further refinements if there is feedback that scaling works better or worse with particular recipe templates.

Recipe templates might also be shared between organisations or categorised on the web in a repository. They might be selected based on user feedback with respect to scaling successes or failures.

Recipe templates may be part of a library and may be retrieved similarly to the parameter evolution information. For example, recipe templates may be stored in a structured data format (e.g. persisted by a serialiser in XML). Recipe templates could equally be stored in a database, spreadsheet, and stored locally, in an organisation file system, in a database within an organisation or on the cloud (remotely).

Recipe, and, thus, recipe templates as well, may comprise marks identifying specific parts of a production process. Exemplarily, a beginning mark and an end mark may enclose a portion of the process. The marks may distinguish portions of the production process that are e.g. more relevant or critical when scaling, as will be explained with reference to the acceptability functions and trajectory comparison below.

Both the parameter evolution information and the recipe templates may be used in a plurality of different scale translations, provided that the production process in question is covered by the steps and the process parameters considered in the parameter evolution information and the recipe templates.

Other inputs required by the method may instead be provided for each specific translation. Indeed, the method further comprises receiving: a source setup specification of a source setup to be used for executing the production process at the source scale, the source setup specification comprising the source scale value; a target setup specification of a target setup to be used for executing the production process at the target scale, the target setup specification comprising the target scale value; a source recipe defining the production process at the source scale.

A setup specification includes information about the setup of the process equipment used for executing the production process, in primis the scale value of the equipment, e.g. the capacity of a bioreactor expressed in litres. Further, the setup specification may include at least one of the components of the setup and its characteristics, e.g. specifying that the equipment comprises an impeller and, optionally, which kind of impeller and so on. Also, other characteristics of the equipment may be indicated by referring to a model of a product, e.g. Sartorius Ambr®. In other words the setup specification describes the equipment used for executing the production process at a given scale, in particular providing information necessary for simulating the process, as will be discussed below.

In particular, the setup specification may specify values for one or more process parameters (e.g. maximum fill volume, minimum fill volume, maximum stirrer speed, maximum gassing rate, minimum gassing rate, lower impeller height, upper impeller height, liquid cross sectional area) that must be fed to a recipe prior to deploying the recipe and/or according to which specific parameter evolution information or recipe templates may be selected.

Examples of a source setup specification and target setup specification are, respectively: Ambr® 250 bioreactor with standard sparger and mammalian impeller, and Sartorius SIR® 50 with ring sparger and two 3-blade impellers.

In addition, a source recipe is provided. In view of the definition of recipe given above, the source recipe is none other than a recipe comprising the plurality of steps (and relative values for process parameters) that define the process as it occurs at the source scale.

An example for a source recipe may correspond to the following procedure: "Fill bioreactor with 0.2 L of given media, heat to 35 degrees, inoculate with clone to a density of 1e6 cells mL-1, incubate stirring at 600 rpm for 36 hrs controlling pH to 7.4 with bottom and top control i.e. addition of acid or base as needed to push pH back to 7.4; maintain temperature; gas at a rate of 0.1 of total volume per minute with air; feed with complex feed for 36 hrs continuing to monitor and control pH, temperature; control DO with stirring and gassing, add inducer to trigger production. Harvest after 36 hrs."

Further, the method comprises receiving at least one acceptability function defining conditions for the values of the process parameter(s) at the source scale and/or at the target scale. Acceptability functions may define conditions both for the recipe parameters and dynamic parameters.

An acceptability function is a parameterised function mapping from a process parameter or a combination of process parameters to a value indicating acceptability. The value for acceptability may be a real number between 0 and 1, i.e. equal to 0 or 1 or greater than 0 and lower than 1. Accordingly, the conditions defined for the values of the process parameters may be binary conditions, in the sense that a value is either considered accepted or not accepted, but they may also be more nuanced conditions, in which a degree of acceptability for a given value is expressed. In other words, the acceptability function may express precise constraints on which values are allowed and/or indicate how fitting a given value is considered to be.

Exemplarily, an acceptability function may fall into two categories, absolute and relative.

A relative acceptability function provides an evaluation of how acceptable a value of a process parameter is when considering the value in relation to other quantities, exemplarily the value for the same process parameter at another scale. In particular, the relative acceptability function may consider the value of the process parameter at the source scale and at the target scale. The source value and the target value may be put in relation to one another in different manners, e.g. considering the difference or the ratio.

An example of a relative acceptability function maps the difference between the source value and the target value for the mixing time to 0 if the mixing time is less at the source than at the target, and to 1 otherwise. Another example maps the difference between the power per volume (PPV) values at source and target scale to a normal distribution.

In other examples, the acceptability function may be a function of two or more process parameters. For example, the difference of the product of cell density and cell activity between source scale and target scale may be mapped to a normal distribution.

Conversely, an absolute acceptability function provides an evaluation of how acceptable a value of a process parameter is when considering the value on its own.

An example of an absolute acceptability function maps a stir speed between 0% and 5% or between 95% and 100% of a maximum possible stir speed (given the target bioreactor) to 0, and a stir speed between 5% and 95% of the maximum possible stir speed to 1. Another example maps the PPV to a normal distribution around a given maximum.

Exemplarily, the at least one acceptability function may be a plurality of acceptability functions comprising at least one absolute acceptability function and at least one relative acceptability function.

The acceptability functions may be grouped according to the scales to which they apply, e.g. according to three groups: a small scale group, an intermediate scale group and a large scale group. As mentioned above, certain scales may fall into more than one group. There may be more than three distinct groups of scales.

The setup specifications, the source recipe and the one or more acceptability functions may be received as input from an external source (e.g. a user and/or a control system configured to execute the production process).

The method further comprises simulating the execution of the production process at the source scale using the source setup specification, the source recipe and the parameter evolution information; and determining, from the simulation, one or more source trajectories for the process parameter(s), wherein a trajectory corresponds to a time-based profile of values recordable during the simulated execution of the production process.

The simulation of the execution of the production process is an imitation of the execution of the production process in the real world performed by means of a computer system. The source setup specification and the source recipe provide initial conditions for the simulation and a description of the process to be simulated, while the parameter evolution information models the evolution of the process with time.

In particular, it is possible to derive values of a process parameter at the different times during the evolution of the process in order to obtain a trajectory. Accordingly, a plurality of source trajectories may be obtained corresponding to a plurality of process parameters as evolved when performing the process at the source scale. In some examples, trajectories may be determined both for recipe parameters and dynamic parameters. In other examples, trajectories may be determined only for dynamic parameters.

Each trajectory may be understood to summarize and provide an overview of the associated process parameter. Each trajectory may be implemented as a curve or graph that describes the time evolution of the process parameter during the simulated execution of the production process. In particular, each trajectory may comprise a plurality of points representing values of a parameter corresponding to different moments in time. For example, a time unit between successive points may be one hour.

The method further comprises performing a target determination step in which the execution of the production process is simulated at the target scale. In order to perform the simulation, one of the plurality of recipe templates is selected and an input value for the at least one variable parameter in the selected recipe template is provided.

The combination of the selected recipe template and the input value for the variable parameter provides a recipe for the target scale that can be used for the simulation, similarly to how the source recipe is used for simulating at the source scale. When there is a plurality of variable parameters, a corresponding plurality of input values is provided, i.e. an input value for each variable parameter, so that the recipe is fully specified.

The recipe template may be selected among all the available recipe templates or within a subgroup of recipe templates pertinent for the particular scaling. "Pertinent" here might mean: appropriate for deployment process or appropriate for organism based on organisational knowledge and/or process knowledge. The selection may be performed by a user or automatically according e.g. to flags present in the recipe templates and indicating their suitability.

The input value may be an educated guess based on process knowledge and it could be part of a set of possible values linked to the specific recipe template. For example, the recipe template may comprise one or more candidate values together with a testing range for each value, so that the input value may be chosen as any value lying in an interval around a candidate values. The candidate values may, thus, be retrieved together with the recipe templates. Alternatively, the input value may be supplied by a user.

The execution of the production process at the target scale is simulated using the target setup specification, the selected recipe template, the input value for the at least one variable parameter and the parameter evolution information. Similarly to what is done for the source scale, one or more target trajectories for the process parameters are then determined.

The target determination step further comprises comparing the source trajectory(ies) and the target trajectory(ies). If only one source trajectory for a given process parameter is determined, only the corresponding target trajectory for the same process parameter may be determined, and the two may be compared. If a plurality of trajectories for the source scale and the target scale are determined, the trajectories are compared pairwise, i.e. the source trajectory for a given process parameter is compared with the target trajectory for the same process parameter.

Exemplarily, the comparison may be carried out by comparing a point on the target trajectory with a corresponding point on the source trajectory. Each trajectory represents a numerical description of a process parameter over time, so that each point on the trajectory is a value of a process parameter at a particular time.

The comparison may e.g. comprise calculating the difference between a point value in the target trajectory and a corresponding (i.e. at the same time) point value in the source trajectory for the same parameter. Other quantitative assessments of the comparison may be performed, such as taking a ratio of the values or combining the values according to given relations.

The target determination step further comprises computing, based on the comparison and on the at least one acceptability function, an acceptability score for the selected recipe template. In particular, the acceptability score is assigned to the combination of the selected recipe template and provided (initial) value(s) for the at least one variable parameter.

The acceptability score indicates a degree of compliance of the production process at the target scale with the conditions of the acceptability function. In other words, the acceptability score provides an evaluation of the combination of the recipe template and value(s) for the variable parameter(s) according to the criteria of acceptability set in the acceptability function(s).

As explained above, the acceptability functions map the process parameters or a combination thereof to acceptability values. Accordingly, one or more applicable acceptability functions are applied to the target trajectories of corresponding process parameters in order to obtain an acceptability score for the combination of the recipe template and value(s) for the variable parameter(s). In other words, the suitability of the recipe template plus values for variable parameters for executing the process at the target scale is assessed via the process parameters trajectories.

By "applicable" is meant that the acceptability function defines conditions for the process parameter to which the source and/or target trajectory corresponds. It should be noted that the process parameter of the trajectories may or may not coincide with the variable parameter. In other words, the acceptability score may express an assessment on the value for the variable parameter in an indirect manner, provided that there is a relation between the trajectory process parameter and the variable parameter, i.e. that they are not completely independent from each other.

In particular, when an absolute acceptability function is applied to a target trajectory, the comparison with the source trajectory may not be needed, i.e. "based on the comparison" may be an optional feature for the computing of (at least part of) the acceptability score.

In other words, the absolute acceptability function may be applied to the values corresponding to the points in the trajectory. When a relative acceptability function is applied to the target trajectory, the acceptability function may be applied to the comparison between the target trajectory and the corresponding source trajectory. In other words, the relative acceptability function may be applied to the comparison between values corresponding to the points in the trajectories, such as the pairwise differences. Further, there may be acceptability functions with higher dimension that require a comparison between multiple source trajectories (e.g. pH and DO) and corresponding (i.e. also pH and DO) target trajectories.

Specifically, if there is only one applicable acceptability function, this is applied to the target trajectory to obtain the acceptability score. In some implementations, this comprises calculating an acceptability value for each time point in the target trajectory and aggregating the acceptability values at different time points to obtain the acceptability score. For example, the aggregation is done by considering the mean (arithmetic or geometric) or the median or the product of the acceptability values, e.g. the acceptability score may be $S1 = \langle S(t) \rangle_t$. Other combinations may be possible.

When there is more than one applicable acceptability function, the acceptability score obtained when applying a single acceptability function to the target trajectory may be a partial acceptability score. All applicable acceptability functions are applied to the target trajectory and the partial acceptability scores obtained by each one of them are aggregated, wherein the aggregation may be done in any of the ways discussed above. For example, the acceptability score may be $S2=\langle S1(\text{acc. func.})\rangle_{acc.func}$.

If there is only one target trajectory, the acceptability score obtained by applying all applicable acceptability functions represents the acceptability score for the target recipe as a whole.

When there is more than one target trajectory, the acceptability scores may be further aggregated. In other words, in case of a plurality of trajectories, an acceptability score is computed for each target trajectory and then these are aggregated for obtaining the acceptability score for the selected recipe template and the provided value(s) for the variable parameter(s).

Exemplarily, the scores obtained for different trajectories are aggregated by computing the exponential of the mean of the log of the scores across the trajectories. In other words, $S3=\exp(\langle \log[S2(\text{traj.})]\rangle_{traj.})$. This ensures that any process that is not performant for any part of the culture (acceptability score=0) will have an aggregate acceptability score of 0, and any process performant perfectly for all of the culture (acceptability score=1) will have an aggregate acceptability score of 1. There are alternative ways of computing the aggregate acceptability score for the recipe template, such as the ones discussed above.

In some examples, in addition to the overall aggregate acceptability score for the recipe template, being e.g. a real number x, with $0 \leq x \leq 1$, an acceptability value may be computed for each time point in the trajectory(ies) and the aggregation may be done separately for each time point. The result would be a function x(t).

To summarize, when a plurality of acceptability functions is received and a plurality of target trajectories are computed, computing the acceptability score may comprise: for each target trajectory of the plurality of target trajectories obtaining a second partial acceptability score by:
selecting one or more applicable acceptability functions;
for each applicable acceptability function performing a calculation step of:
calculating an acceptability value based on the acceptability function for each time point in the target trajectories;
aggregating the acceptability values at the different time points to obtain a first partial acceptability score;
if there is a single applicable acceptability function, setting the second partial acceptability score to the first partial acceptability score;
if there is a plurality of applicable acceptability functions, aggregating the first partial acceptability scores for all applicable acceptability functions to obtain the second partial acceptability score;
and aggregating the second partial acceptability scores for all target trajectories to obtain the acceptability score.

As explained above, recipe templates may comprise marks identifying specific parts of a production process. Exemplarily, a beginning mark and an end mark may enclose a portion of the process. The marks allow an acceptability function to apply to part or all of a trajectory.

For example, in the recipe template the start of the batch phase and the end of the batch phase may be marked. When marks are present in the recipe template, all or a subset of the acceptability functions should be applied e.g. only to the interval between start and end batch to the target trajectories. In other words, some acceptability functions may be applied only to a phase, e.g. the batch phase, and other acceptability functions may be applied only to another phase, e.g. the fed phase. For example, during the batch phase, the gassing may be set to constant in the recipe template and an acceptability function that makes the acceptability score dependent on the percentage of dissolved oxygen is applied only to the batch phase interval in the trajectories, since the goal is to ensure constant gassing results in similar dissolved oxygen environments during batch phase.

When a (relative) acceptability function is applied to a comparison between source and target trajectories between two marks, time is optionally scaled between the source and target trajectories so that the interval between the marks is the same.

For example, in the simulation at the source scale, the batch phase starts at t=2 and ends at t=12; at target scale, the batch phase starts at t=2 and ends at t=22. In trajectory comparison between these marks either: t=5 in the source trajectory is compared with t=5 in the target trajectory (i.e. not scaled) or t=5 in the source trajectory is compared with t=8 in the target trajectory (i.e. scaled, each unit in target is worth 2 in the source, 3 time units have passed between start of batch).

Finally, the target determination step comprises computing an optimal value for the at least one variable parameter in the selected recipe template by optimising the acceptability score and/or computing an acceptable range for the at least one variable parameter, wherein values within the acceptable range yield an acceptability score above a specific threshold.

The acceptability score computed as explained above yields a number whose value is dependent, among others, on the value(s) assigned to the variable parameter(s) in the selected recipe template. Thus, the acceptability score may be seen as a function of the one or more variable parameters, hereafter called "score function". In the case of a plurality of variable parameters present in the selected recipe template, the score function is a multi-variable function of the variable parameters.

The score function may be optimised to find the best input values for the variable parameters, i.e. those values for which the process at the target scale is most similar to the process at the source scale and most successful according to the criteria specified by the acceptability functions. Finding the optimal value(s) for the variable parameter(s) is an optimisation problem in which the score function is maximised or minimised by systematically choosing input values from within an allowed set and computing the value of the score function. Depending on the number of variable parameters, the optimisation problem may be a multi-dimensional problem. The allowed set may be specified in the recipe template, as mentioned above, or may be otherwise determined. In some cases, there may be more than one optimal value that optimises the score function. If the score function assumes real values between 0 and 1, and 1 is assigned to perfect acceptability, then the score function must be maximised. Examples of optimisation algorithms are the Nelder-Mead method and the steepest descent method. The result of optimising is that the parameter value or the combination of parameter values that give the best (e.g. highest score) for the selected recipe template is found. In some cases, it may be necessary to use multiple starting values for optimisation, as the space being explored may be highly non-linear and may exhibit multiple local optima.

In addition or alternatively to finding the optimal value(s) for the variable parameter(s), acceptable range(s) may be found by constraining the score function to assume a value (i.e. the acceptability score) above a specific predetermined or predeterminable threshold. There may be more than one acceptable range for a given variable parameter. The threshold may be input by a user or may be set or derived based on the best value obtainable for the acceptability score, e.g. a fraction of the best value such as 70%, 80% or 90% or set based on absolute criteria on the acceptability score, e.g. it has to be at least 0.5 or 0.6 or 0.7. In particular, the term "range" should be construed broadly to encompass multi-dimensional results.

Accordingly, the result of the target determination step may be a single point in the variable parameter space and/or a curve or surface in the variable parameter space. Mathematically speaking, this will correspond in the exemplary case to the union of a set of arbitrary dimensional manifolds.

However, as explained above, a given acceptability score is not just the result of the input values fed to a selected recipe template, but also of the choice of the recipe template itself. Therefore, the target determination step may be repeated for at least another recipe template, if there is more than one pertinent recipe template. Accordingly, the step of "repeating the target determination step for at least another pertinent recipe template" may be optional. In particular, the target determination step may be repeated for all recipe templates in the library or only for the recipe templates in the subset of pertinent recipe templates discussed above.

The method further comprises selecting at least one of the plurality of recipe templates as target recipe based on the acceptability scores computed for one or more recipe templates. In particular, the one or more recipe templates selected as target recipe are selected together with the optimal input value(s) and/or the acceptable range(s) for the input value(s).

Once the target determination step has been completed for all the recipe templates for which it is supposed to be performed, each recipe template has an (optimal) acceptability score associated with an optimal input value and/or a plurality of acceptability scores above a given threshold associated with a range of input values.

Therefore, one or more candidates for the target recipe, which will specify how to execute the process at the target scale for the actual deployment, may be chosen among the combinations recipe template plus input value(s) based on the acceptability scores computed when optimising and/or when setting a minimum threshold. In some examples, a single target recipe may be selected while in other examples a plurality of target recipes may be given. In particular, a single recipe template with a plurality of acceptable input values for a single variable parameter (e.g. more than one optimal value or an acceptable range) may originate a plurality of target recipes. Similarly, a plurality of recipe templates with good acceptability scores may originate a plurality of target recipes.

According to an exemplary implementation, the method may further comprise outputting the one or more target recipes in the form of recipe template(s) plus input value(s). Additionally, the corresponding "best" predicted trajectory(ies) at the target scale and/or the acceptability score(s) may be output. In particular, if also the time-dependent acceptability score x(t) has been computed, as discussed above, this could also be output.

In some implementations, the target recipe(s) obtained by the above-explained selection may be cast in a form that an automated system can handle, for example an "experiment protocol" on Ambr® 15 or Ambr® 250. The method may further comprise providing the target recipe to a target control system; and executing, by the target control system, the production process at the target scale based on the target recipe. The identified scaled process conditions may be transferred either manually or automatically between bioreactor configurations.

In other words, the target recipe(s) with relative input value(s) as selected by the above-described method may be fed directly to a target control system configured to control the target setup equipment to carry out the process at the target scale. If more than one target recipe (see above) is provided to the target control system, the target control system may select only one target recipe e.g. based on certain priors such as existing configuration of the target setup, or may execute the production process multiple times.

When the production process is executed in the real world at the target scale, the results may be used to provide feedback. In some implementations, the method may further comprise evaluating the performance of the production process at the target scale; and modifying the at least one acceptability function based on the evaluation.

The performance of the production process may e.g. be evaluated by using the quality attributes defined above. Modifying the at least one acceptability function based on the evaluation may include assigning weights to the acceptability functions, so that they become more or less relevant in determining the acceptability score. For example, if the scaling resulted in a good performance, the acceptability functions involved may be given a greater weight. Conversely, if the scaling resulted in a poor performance, the acceptability functions involved may be given a lower weight. In other examples, the form of the acceptability functions may be modified, e.g. by substituting a normal distribution with a different distribution or by changing the range of values of a process parameter that are mapped to 0 by the acceptability function.

Another example for feedback is to use the predicted target trajectories and the actual trajectories and modify the parameters for the simulation when there are discrepancies between the predicted and actual trajectories. The means of modifying these parameters is that of non-linear fitting i.e. minimisation of differences between observed and expected.

Yet other feedback mechanisms may be implemented, such as in order to improve the parameter evolution information.

In some implementations, the source recipe defining the production process at the source scale may be obtained by:
defining an aim quantity characterizing the production process at the source scale;
executing, by a source control system, the production process multiple times at the source scale while varying the process parameters and/or the process steps;
selecting, for defining the source recipe, a process based on the result for the aim quantity given by the process parameters and the process steps.

The aim quantity may be related to the product and/or to other aspects of the process. For example, the aim quantity may be one or a combination of the quality parameters, or may be defined otherwise. The production process may be repeated a plurality of times, since e.g. at small scale it is not too expensive, in order to find the best combination of process steps specified by given process parameters, wherein the best combination is the one that optimises, e.g. maximises, the aim quantity.

Examples of aim quantities that would be maximised include but are not limited to one or more of the following:
Total quantity or quantity per unit volume
Quality (chemical composition of product, protein structure (primary, secondary and tertiary structures), glycsolyation patterns)
Purity (quantity of product relative to similar molecules)
Release of product from cell wall, cytoplasm or other cell compartments,
Release of cell lysis being beneficial for product release into media
Throughput (that is, the inverse of cycle time, that is, minimising culture period)
Ability to detect process deviations early and correct (e.g. might point towards increased sampling)

Examples of aim quantities that would be minimised include but are not limited to one or more of the following:
Cell debris
Presence of molecules, cell components or cell that interfere with purification
Shear or chemical damage to product
Media cost (either total media used, or expensive components of media)
Energetic cost (especially at larger scales)
Risk of process failure (i.e. the degree to which small fluctuations e.g. in bioreactor or cell performance might push the process out of the operational region)

The recipe-scaling method illustrated above for scaling from a source scale to a target scale can be generalized for the so-called train scaling, i.e. for scaling from a source scale to a final target scale passing through one or more intermediate target scales. Conventionally, each transition in the train scaling is treated separately. Instead, according to the present invention and in particular thanks to the acceptability function, the train scaling is performed considering all passages from one scale to another at the same time. In other words, the train scaling is treated as a single, composite process instead of artificially separating it into pairwise scalings. Thus, the chances of successful performances of the process at any subsequent scale are increased.

The method as described above is naturally extended to the train scaling scenario. When the scaling method is applied to a train scaling comprising one or more intermediate target scales, one or more additional simulations need to be run for the one or more intermediate target scales, which requires corresponding intermediate target setups and, especially, corresponding input values for the variable parameters in the recipe templates. Indeed, one of the goals of the method for train scaling is to obtain a target recipe for each of the intermediate target scales and the final target scale. This means that, once a pertinent recipe template is selected, its one or more variable parameters are tentatively populated by one or more sets of input values, respectively. In other words, for each variable parameter, a plurality of input values, each corresponding to a target scale, is provided. For example, taking a case with two intermediate target scales between the source scale and the final target scale, a first, second and third input values are provided for the variable parameter; the first input value may provide an educated guess for the value of that variable parameter at the first intermediate target scale, the second input value may provide an educated guess for the value of that variable parameter at the second intermediate target scale and the third input value may provide an educated guess for the value of that variable parameter at the final target scale. Accordingly, the simulation run for each scale is based on the combination of the recipe template and the corresponding input value provided for that scale.

Based on the plurality of simulations, trajectories for the intermediate target scales are determined, in addition to those for the source and final target scales. The trajectories at different scales are then compared pairwise and also in higher-cardinality combinations (e.g. three trajectories at three different scales are compared together or four trajectories at four different scales are compared together and so on). For example, the comparison of three trajectories may e.g. comprise calculating the difference between a point value in the final target trajectory and the sum of corresponding (i.e. at the same time) point values in the source trajectory and in the intermediate target trajectory for the same parameter. Other quantitative assessments of the comparison may be performed.

The at least one acceptability function for the train scaling may, in particular, define conditions for the values of the process parameters at any single scale and/or at any number of scales. In particular, there may be absolute acceptability functions defining conditions for the process parameters at any single scale taken alone and/or there may be relative acceptability functions defining conditions on relations between values at two or more different scales. The score will in this case be derived as an aggregate of the output of acceptability functions from a plurality of scale combinations.

Finally, similarly to the two-scale translation, an optimisation problem is solved. The difference is that the dimensionality of the optimisation problem is higher in the train scaling. If a simple example in which the selected recipe template has only one variable parameter is considered, the dimensionality of the optimisation problem of the acceptance score function for that recipe template is one. In the case of train scaling, the dimensionality is increased depending on the number of intermediate target scales. If there is one intermediate target scale, the optimisation process has to find at the same time an optimal value for the variable parameter for the intermediate target scale and an optimal value for the variable parameter for the final target scale, i.e. the presence of one intermediate target scale has increased of one the dimensionality of the problem. If there are two intermediate target scales, the dimensionality is increased by two, for the simple example above. Generally, if the dimensionality of the optimisation problem in the two-scale translation is D1 and the number of intermediate target scales plus final target scale is T, the dimensionality of the optimisation problem in the train scaling with T-1 intermediate target scales will be $D2=D1*T$. Accordingly, the number of "constraints" imposed by the acceptability functions must be sufficient for making the optimisation problem determined. This may translate for example into optimising at least two acceptability score functions simultaneously, which may e.g. be combined by multiplication. It may also result in the output of the optimisation being a range of possibilities for intermediate scales, all of which share the maximal value of the aggregated score.

Similar considerations apply, with due differences, for the acceptable ranges.

Therefore, at least one result of the method for train scaling is to provide one or more target recipes for each one of the intermediate target scales and the final target scale. All other aspects illustrated for the two-scale translation, when applicable, can be implemented for the train scaling, such as outputting the target recipe(s) and also outputting the acceptability scores and the predicted trajectories, as well as the feedback mechanisms.

A recap of the method for train scaling for the case of one intermediate target scale is found below, however it is clear that it can be extended to any number of intermediate target scales.

A computer-implemented method of scaling a production process to produce a chemical, pharmaceutical and/or biotechnological product, the scaling being from a source scale to an intermediate target scale to a final target scale, wherein the production process is defined by a plurality of steps specified by one or more process parameters controlling an execution of the production process, the method comprising:
  retrieving:
    parameter evolution information that describes the time evolution of the process parameter(s);
    a plurality of recipe templates, wherein:
  a recipe comprises the plurality of steps defining the production process, and
  a recipe template is a recipe in which at least one of the process parameters specifying the plurality of steps is a parameter being variable and having no predetermined value at the outset;
  receiving:
    a source setup specification of a source setup to be used for executing the production process at the source scale, the source setup specification comprising the source scale value;
    an intermediate target setup specification of an intermediate target setup to be used for executing the production process at the intermediate target scale, the intermediate target setup specification comprising the intermediate target scale value;
    a final target setup specification of a final target setup to be used for executing the production process at the final target scale, the final target setup specification comprising the final target scale value;
    a source recipe defining the production process at the source scale;
    at least one acceptability function defining conditions on the values of the process parameter(s) when the values are considered singularly at any one of the source scale, intermediate target scale and final target scale and/or when the values at any one scale are considered in relation to corresponding values at any another one or more scales;
  simulating the execution of the production process at the source scale using the source setup specification, the source recipe and the parameter evolution information;
  determining, from the simulation, one or more source trajectories for the process parameter(s), wherein a trajectory corresponds to a time-based profile of values recordable during the simulated execution of the production process;
  performing a target determination step comprising:
    selecting a recipe template pertinent to the production process out of the plurality of recipe templates;
    providing a first input value for the at least one variable parameter in the selected recipe template;
    providing a second input value for the at least one variable parameter in the selected recipe template;
    simulating the execution of the production process at the intermediate target scale using the intermediate target setup specification, the selected recipe template, the first input value for the at least one variable parameter and the parameter evolution information;
    determining, from the simulation, one or more intermediate target trajectories for the process parameters;
    simulating the execution of the production process at the final target scale using the final target setup specification, the selected recipe template, the second input value for the at least one variable parameter and the parameter evolution information;
    determining, from the simulation, one or more final target trajectories for the process parameters;
    making a first, a second and a third pairwise comparison between any two of the source trajectory(ies), the intermediate target trajectory(ies) and the final target trajectory(ies), and making a three-wise comparison among the source trajectory(ies), the intermediate target trajectory(ies) and the final target trajectory(ies);
    computing an acceptability score based on at least two comparisons and on the at least one acceptability function;
    computing a first optimal value and a second optimal value for the at least one variable parameter by optimising the acceptability score and/or computing a first acceptable range and a second acceptable range for the at least one variable parameter, wherein values within the first acceptable range and values within the second acceptable range yield an acceptability score above a specific threshold;
  if there is at least another pertinent recipe template, repeating the target determination step for at least another pertinent recipe template;
  selecting at least one of the plurality of recipe templates and corresponding computed value(s) for variable parameter(s) as target recipe based on the acceptability scores computed for one or more of recipe templates.

In particular, computing an acceptability score may comprise computing any combination of:
  a first acceptability score for the selected recipe template based on the first pairwise comparison and on the at least one acceptability function;
  a second acceptability score for the selected recipe template based on the second pairwise comparison and on the at least one acceptability function;
  a third acceptability score for the selected recipe template based on the third pairwise comparison and on the at least one acceptability function;
  a fourth acceptability score for the selected recipe template based on the three-wise comparison and on the at least one acceptability function;
  and computing the optimal values/acceptable ranges may comprise:
computing a first optimal value and a second optimal value for the at least one variable parameter in the selected recipe template by simultaneously optimising at least two of the first acceptability score, the second acceptability score, the third acceptability score and the fourth acceptability score and/or
computing a first acceptable range and a second acceptable range for the at least one variable parameter, wherein values within the first acceptable range yield any one of a first acceptability score, a second acceptability score, a third acceptability score and a fourth acceptability score above a respective first, second, third or fourth specific threshold and values within the second acceptable range yield any other one of a first acceptability score, a second acceptability score, a third acceptability score and a fourth acceptability score above a respective first, second, third or fourth specific threshold.

In order to better illustrate how the train scaling method is just an extension of the two-scale method, reference is made to the following wording.

The computer-implement method for translating from a source scale to a target scale, wherein:
the target scale is a final target scale;
there is an intermediate target scale;
the at least one acceptability function further or alternatively defines conditions for the values of the process parameters at the intermediate target scale and/or values of the process parameters at any two scales in relation to each other and/or values of the process parameters at all scales in relation to each other;
the input value for the at least one variable parameter is a first input value;
the comparison between the source trajectory(ies) and the final target trajectories is a first pairwise comparison;
the optimal value for the at least one variable parameter is a first optimal value and the acceptable range for the at least one variable parameter is a first acceptable range;
wherein the method further comprises:
retrieving an intermediate target setup specification of an intermediate target setup to be used for executing the production process at the intermediate target scale, the intermediate target setup specification comprising the intermediate target scale value; and
the target determination step further comprises:
providing a second input value for the at least one variable parameter in the selected recipe template;
simulating the execution of the production process at the intermediate target scale using the target setup specification, the selected recipe template, the second input value for the at least one variable parameter and the parameter evolution information;
determining, from the simulation, one or more intermediate target trajectories for the process parameters;
making a second pairwise comparison between the source trajectory(ies) and the intermediate target trajectory(ies) and a third pairwise comparison between the intermediate target trajectory(ies) and the final target trajectory(ies), and making a three-wise comparison among the source trajectory(ies), the intermediate target trajectory(ies) and the final target trajectory(ies);
wherein computing the acceptability score is performed based on any combination of the first, second, third pairwise comparison and three-wise comparison, and wherein the first optimal value is computed simultaneously/together with a second optimal value for the at least one variable parameter in the selected recipe template by optimising the acceptability score and/or
the first acceptable range is computed simultaneously/together with a second acceptable range for the at least one variable parameter, wherein values within the first acceptable range and values within the second acceptable range yield an acceptability score above a specific threshold.

In another aspect of the invention, a computer-implemented method of scaling a state of a production equipment for a production process to produce a chemical, pharmaceutical and/or biotechnological product, the scaling being from a source scale to a target scale, wherein the state is defined by a set of state parameters describing a condition and/or a behaviour of the production equipment, is provided. This method is also called instantaneous or time-point scaling and achieves the object of identifying best match parameters for a given time-point between a process at one scale and at another scale.

A state of the production equipment may indicate a static or dynamic condition, e.g. how much a bioreactor is filled, and/or a behaviour of the production equipment, e.g. the stirring speed at which an impeller operates. The state parameters are quantities that define such condition/behaviour, in particular by quantifying it when assuming a given value. Since the state of the production equipment is also influenced by its environment, in some cases the state parameters may include parameters that relate indirectly to the production equipment by describing the environment.

The state parameters may be set e.g. by an operator or by a control system. Exemplarily, the state parameters for a bioreactor may include but are not limited to: stir speed, gassing, fill volume and indications about which gas to add. In particular, the state parameters may coincide or be a proper subset of the recipe parameters defined above.

Although in the following it will be mostly referred to a plurality of state parameters, the set may also have dimension 1, namely there may be only one state parameter.

The method comprises retrieving mapping information that describes how the state parameters relate to a set of derived parameters.

The mapping information may include theoretical equations and/or fitted relations that links one or more state parameters to one or more derived parameters. While the state parameters relate rather to how the production equipment is setup, the derived parameters relate more to the production equipment in the context of the production process being performed with it. In other words, the derived parameters may be quantities that arise during the production process and that may not be controlled by an external input.

Exemplarily, the derived parameters for a bioreactor may include but are not limited to one or more: tip speed, $k_La$, mixing time, power input, Reynold's number, Froude number, minimum eddy size and superficial gas velocity. In particular, the derived parameters may coincide or be a proper subset of the dynamic parameters defined above.

It should be noted that the derived parameters provide a static description, i.e. their values are considered at a given time point and not as they evolve during the process. The derived parameters therefore represent a "snapshot" of a process. In scale translation in this mode of operation, a user may make use of a range of time-points, or "snapshots" within the process, and ensure accuracy of scale translation in all of these.

Also the set of derived parameters may have dimension 1.

The mapping information may exemplarily be dependent on the specific production equipment, so that it may comprise a plurality of relations between e.g. the same state parameter and the same derived parameter, with each different relation applying to a specific production equipment.

The mapping information may be retrieved in any of the manner illustrated to the parameter evolution information.

The method further comprises receiving:
a source setup specification of a source setup used for executing the production process at the source scale, the source setup specification comprising the source scale value;

a target setup specification of a target setup used for executing the production process at the target scale, the target setup specification comprising the target scale value;

a first set of state parameters at the source scale;

a second set of state parameters at the target scale, wherein at least one of the state parameters at the target scale is a parameter being variable and having no predetermined value at the outset;

at least one acceptability function defining conditions on the values of the state parameter(s) and/or the values of the derived parameter(s) at the source scale and/or at the target scale.

The setup specifications are the same as those discussed for the recipe scaling above. Also the scope and form of the acceptability function(s) is the same as discussed above, in particular there may be relative and absolute acceptability functions. Relative acceptability functions may define conditions on values of the state parameters at the source scale and at the target scale and/or conditions on values of the derived parameters at the source scale and at the target scale.

Further, a first set of state parameters (i.e. the values thereof) is provided, which describes the state of the production equipment at the source scale. Similarly, a second set of state parameters for the target scale is provided. However, the state at the target scale is not completely determined, since one of the objectives of the method is to find one or more optimal states at the target scale that correspond to the state at the source scale. Accordingly, at least one of the state parameters for the target scale in the second set is left free, in the sense that its value or their values is not fixed but can be modified in order to arrive at the best solution. The role of the variable parameters in the set of state parameters is the same as the role of the variable parameters in the recipe templates above.

The method further comprises calculating a first set of derived parameters at the source scale using the first set of state parameters, the source setup specification and the mapping information; providing an input value for the at least one variable parameter in the second set of state parameters; calculating a second set of derived parameters at the target scale using the second set of state parameters, the input value, the target setup specification and the mapping information.

As explained, the mapping information allows to derive the derived parameters from the state parameters. Accordingly, using the mapping information and the source setup specification, a first set of derived parameters at the source scale can be calculated. The calculation may be performed analytically or by means of a numerical simulation.

The source setup specification may be needed for selecting the appropriate relations for the given source production equipment. Further or alternatively, some of the derived parameters may be obtained based on features/quantities contained in the setup specification, such as regarding the geometry of the production equipment.

Similarly, the second set of state parameters is used together with one or more "guessed" input values for the one or more variable parameters to derive a second set of derived parameters.

The method further comprises comparing the first set of state parameters with the second set of state parameters and/or comparing the first set of derived parameters and the second set of derived parameters.

The comparison may e.g. comprise calculating the difference between a state parameter in the second set, i.e. at the target scale, and the same parameter in the first set, i.e. at the source scale. The same holds for the derived parameters. Other quantitative assessments of the comparison may be performed, such as taking a relative difference, i.e. absolute value of (value in source−value in target)/(maximum (value in source, value in target)), a ratio of the values or combining the values according to given relations.

Finally, the method comprises computing, based on the comparison and on the at least one applicable acceptability function, an acceptability score for the second set of state parameters; computing an optimal value for the at least one variable parameter by optimising the acceptability score and/or computing an acceptable range for the at least one variable parameter, wherein values within the acceptable range yield an acceptability score above a specific threshold.

The optimisation of the acceptability score function corresponds to the one described for the recipe scaling. In this case, the acceptability score function is a function of the at least one variable parameter in the second set of state parameters. Since there are no trajectories, the computation of the acceptability score is simplified.

If there is a plurality of acceptability functions and a plurality of variable parameters, computing the acceptability score comprises:

for each pertinent variable parameter of the plurality of variable parameters obtaining a partial acceptability score by:

selecting one or more applicable acceptability functions;

for each applicable acceptability function calculating an acceptability value;

if there is a single applicable acceptability function, setting the acceptability value to the partial acceptability score;

if there is a plurality of applicable acceptability functions, aggregating the acceptability values for all applicable acceptability functions to obtain the partial acceptability score; and aggregating the partial acceptability scores for all variable parameters to obtain the acceptability score.

Aggregating can be done as explained previously, e.g. by taking the arithmetic or geometrical mean.

One of the results of the method is, thus, an optimised set of state parameters for the target scale. This may be output and e.g. automatically fed to a control system for setting up the production equipment at the target scale. Other results that may be output include the second set of derived parameters at the target scale and the acceptability score.

It is evident that the time-point scaling may be described as a special case of the recipe scaling, with some special conditions applying. In particular, the parameter evolution information includes only relations between parameters and no equations for time evolution, the recipes and recipe templates only comprise parameters but no process steps.

Thus, the same principles explained above apply for extending the time-point scaling to a train scaling. In the particular case of one intermediate target scale, the method would comprise:

retrieving mapping information that describes how the state parameters relate to a set of derived parameters;

receiving:

a source setup specification of a source setup used for executing the production process at the source scale, the source setup specification comprising the source scale value;

an intermediate target setup specification of an intermediate target setup to be used for executing the production process at the intermediate target scale, the intermediate target setup specification comprising the intermediate target scale value;

a final target setup specification of a final target setup used for executing the production process at the final target scale, the final target setup specification comprising the final target scale value;

a first set of state parameters at the source scale;

a second set of state parameters at the intermediate target scale, wherein at least one of the state parameters at the intermediate target scale is a first parameter being variable and having no predetermined value at the outset;

a third set of state parameters at the final target scale, wherein at least one of the state parameters at the final target scale is a second parameter being variable and having no predetermined value at the outset;

at least one acceptability function defining constraints on the values of the state parameter(s) and/or the values of the derived parameter(s) at the source scale and/or at the intermediate target scale and/or at the final target scale;

calculating a first set of derived parameters at the source scale using the first set of state parameters, the source setup specification and the mapping information;

providing a first input value for the at least one first variable parameter in the second set of state parameters;

calculating a second set of derived parameters at the intermediate target scale using the second set of state parameters, the first input value, the intermediate target setup specification and the mapping information;

providing a second input value for the at least one second variable parameter in the third set of state parameters;

calculating a third set of derived parameters at the final target scale using the third set of state parameters, the second input value, the final target setup specification and the mapping information;

making a plurality of pairwise comparisons within all pairs of any two of the first, second and third set of state parameters and/or within all pairs of any two of the first, second and third set of derived parameters, and making at least one three-wise comparison among the first, second and third set of state parameters and/or among the first, second and third set of derived parameters;

computing an acceptability score based on at least two comparisons and on the at least one acceptability function;

computing a first optimal value for the at least one first variable parameter and a second optimal value for the at least one second variable parameter by optimising the acceptability score and/or computing a first acceptable range for the at least one first variable parameter and a second acceptable range for the at least one second variable parameter, wherein values within the first acceptable range and values within the second acceptable range yield an acceptability score above a specific threshold.

It is clear that the above method can be generalised to any arbitrary number of intermediate target scales.

According to another aspect, a computer program product is provided. The computer program product comprises computer readable instructions, which, when loaded and executed on a computer system, cause the computer system to perform operations as described above. The computer program product may be tangibly embodied in a computer readable medium.

According to yet another aspect of the invention, a computer system operable to scale a production process to produce a chemical, pharmaceutical and/or biotechnological product from a source scale to a target scale is provided. The production process is defined by a plurality of steps specified by one or more process parameters controlling an execution of the production process and the computer system comprises:

a retrieving module configured to retrieve:
  parameter evolution information that describes the time evolution of the process parameter(s);
  a plurality of recipe templates, wherein:
    a recipe comprises the plurality of steps defining the production process, and a recipe template is a recipe in which at least one of the process parameters
    specifying the plurality of steps is a parameter being variable and having no predetermined value at the outset;

a receiving module configured to receive:
  a source setup specification of a source setup to be used for executing the production process at the source scale, the source setup specification comprising the source scale value;
  a target setup specification of a target setup to be used for executing the production process at the target scale, the target setup specification comprising the target scale value;
  a source recipe defining the production process at the source scale;
  at least one acceptability function defining conditions for the values of the process parameter(s) at the source scale and/or at the target scale; and a computing module configured to:
  simulate the execution of the production process at the source scale using the source setup specification, the source recipe and the parameter evolution information;
  determine, from the simulation, one or more source trajectories for the process parameter(s), wherein a trajectory corresponds to a time-based profile of values recordable during the simulated execution of the production process;
  perform a target determination step comprising:
    selecting one of the plurality of recipe templates;
    providing an input value for the at least one variable parameter in the selected recipe template;
    simulating the execution of the production process at the target scale using the target setup specification, the selected recipe template, the input value for the at least one variable parameter and the parameter evolution information;
    determining, from the simulation, one or more target trajectories for the process parameters;
    comparing the source trajectory(ies) and the target trajectory(ies);
    computing, based on the comparison and on the at least one acceptability function, an acceptability score for the selected recipe template;
    computing an optimal value for the at least one variable parameter in the selected recipe template by optimising the acceptability score and/or computing an acceptable range for the at least one variable parameter, wherein values within the acceptable range yield an acceptability score above a specific threshold;

select at least one of the plurality of recipe templates as target recipe based on the acceptability scores computed for one or more recipe templates.

The computer system may particularly comprise a memory and a processor to operate the modules. The retrieving module, the receiving module and the computing module may be separate entities or may at least partly overlap with each other.

Further, the computer system may be configured to interface with a target control system and/or a source control system via a network, shared disk, or database system, wherein the control systems control the execution of the production process in the real world at the source and target scales. The interface may particularly allow transfer of data and/or commands.

In some examples, the computer system may coincide with at least one of the target control system and source control system.

The computer system above may also be suitable, mutatis mutandis, for carrying out a recipe train scaling, a time-point scaling and a time-point train scaling as illustrated above.

In conclusion, the invention particularly provides a means of scaling that treats the process as a whole, so that optimisation of a match between scales does not favour parts of the process at the expense of the whole. This is the case both for recipe scaling and time-point scaling. Further, means of assessing risk across potential operational space are provided by the acceptability score, rather than just optimal values for the process parameter at the target scale.

The acceptability functions particularly allow sensitivities to be expressed, i.e. knowledge about what matters for the process parameters, and taken into account in the scaling process. Further, the parameter evolution information particularly brings together experimental bioreactor data with cell culture models in order to accurately simulate a production process involving several process parameters.

Finally, it is possible to reconcile multiple scales at the same time. Indeed, a full scaling train can be optimised in a single shot, so that, at each stage of deployment onto hardware during scaling, there is a good established prospect of being able to proceed further in the event of success.

The subject matter described in this application can be implemented as a method or on a device, possible in the form of one or more computer program products. The subject matter described in the application can be implemented in a data signal or on a machine readable medium, where the medium is embodied in one or more information carriers, such as a CD ROM, a DVD ROM, a semiconductor memory, or a hard disk. Such computer program products may cause a data processing apparatus to perform one or more operations described in the application.

In addition, subject matter described in the application can be implemented as a system including a processor, and a memory coupled to the processor. The memory may encode one or more programs to cause the processor to perform one or more of the methods described in the application. Further subject matter described in the application can be implemented using various machines.

BRIEF DESCRIPTION OF THE DRAWINGS

Details of exemplary embodiments are set forth below with reference to the exemplary drawings. Other features will be apparent from the description, the drawings, and from the claims. The drawings should be understood as exemplary rather than limiting, as the scope of the invention is defined by the claims.

DETAILED DESCRIPTION OF EMBODIMENTS

In the following text, a detailed description of examples will be given with reference to the drawings. It should be understood that various modifications to the examples may be made. In particular, one or more elements of one example may be combined and used in other examples to form new examples.

Figure 1:
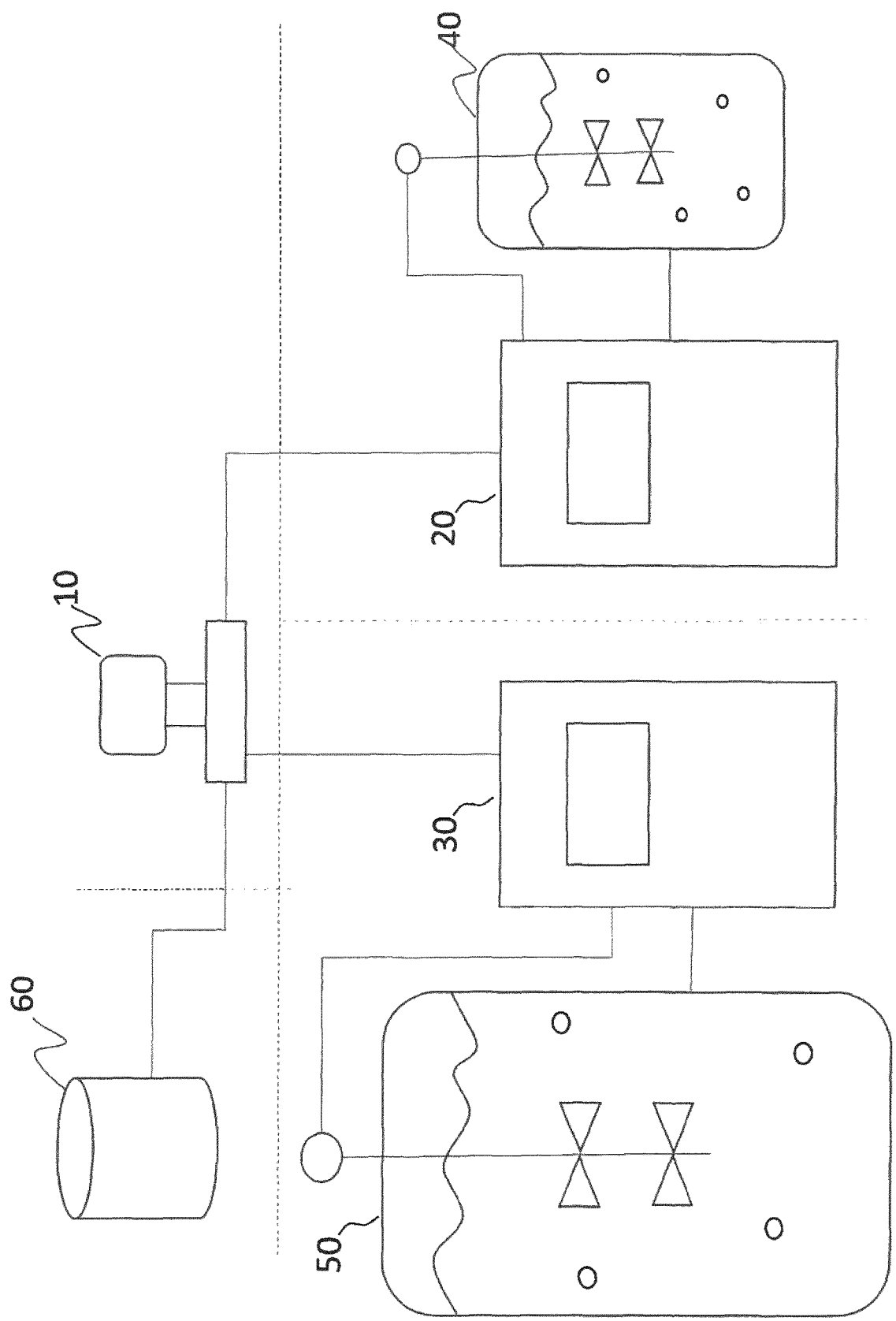
FIG. 1 shows a computer system for scaling a production process to produce a chemical, pharmaceutical, or biotechnological product.

FIG. 1 shows a computer system 10 for scaling a production process to produce a chemical, pharmaceutical, or biotechnological product.

The computer system 10 may include a processing unit, a system memory, and a system bus. The system bus couples various system components including the system memory to the processing unit. The processing unit may perform arithmetic, logic and/or control operations by accessing the system memory. The system memory may store information and/or instructions for use in combination with the processing unit. The system memory may include volatile and non-volatile memory, such as a random access memory (RAM) and a read only memory (ROM).

The computer system 10 may further include a hard disk drive for reading from and writing to a hard disk (not shown), and an external unit drive for reading from or writing to a removable unit. The drives and their associated computer-readable media provide nonvolatile storage of computer readable instructions, data structures, program modules and other data for the personal computer 920. The data structures may include relevant data for the implementation of the method as described above.

A number of program modules may be stored on the hard disk, external disk, ROM or RAM, including an operating system (not shown), one or more application programs, other program modules (not shown), and program data. The application programs may include at least a part of the functionality as described below.

A user may enter commands and information into the computer system 10 through input devices such as keyboard and mouse. A monitor or other type of display device is also connected to the system bus via an interface, such as a video input/output.

The computer system 10 may communicate with other electronic devices. To communicate, the computer system 10 may operate in a networked environment using connections to one or more electronic devices.

In particular, the computer system may interface and communicate with a source control system 20 and a target control system 30. The computer system 10 may be operable, possibly in conjunction with other devices, to scale a production process.

The source control system 20 may be connected to a bioreactor 40 constituting the source equipment for performing the production process at the source scale. Similarly, the target control system 30 may be connected to a bioreactor 50 constituting the target equipment for performing the production process at the target scale. Although the bioreactor 40 is shown as being smaller than the bioreactor 50, the situation could be reversed.

The source control system 20 and the target control system 30 may be located in the same production facility or in different production facilities at different locations. The source control system 20 and the target control system 30 may be different entities or may coincide, i.e. be a single entity (not shown).

The control systems 20, 30 and the computer system 10 may be located in different rooms of the same facility or in different buildings on a corporate campus. The computer system 10 may be a separate entity from the control systems 20, 30. In other examples (not shown) the computer system 10 may coincide with at least one of the source control system 20 and the target control system 30.

In some examples, a database 60 may be provided. The database may be connected to a network, such that the database is accessible by multiple devices/users. The database may be implemented as a cloud database, i.e. a database that runs on a cloud computing platform. In other words, the database may be accessible over the Internet via a provider that makes shared processing resources and data available to computers and other devices on demand. The database may be implemented using a virtual machine image or a database service. The database may use an SQL based or NoSQL data model.

The database 60 may store any of: sets of values for process parameters, recipes, recipe templates, parameter evolution information, setup specifications, acceptability functions. The database 501 may be accessible from the process control device 503 via the Internet.

Communications between the database 60 and the computer system 10 may be secured, e.g. via Internet protocol security (IPSEC) or other security protocols. A virtual private network (VPN) may also be used.

The database 60 may be hosted by a service provider, possibly on a virtual machine, and may be accessible by various users from multiple organizations, possibly located in a variety of different geographic locations around the world. Alternatively, the database 60 may be hosted locally, e.g. in the computer system 10. Accordingly, the computer system 10 and the database 60 may or may not be located in physical proximity. In particular, the database 60 may be located in a location that is geographically distant (e.g. on another continent) from the computer system.

An example of a production process that is scaled by the computer system 10 may be a fed-batch process comprising the following phases:
 add media to bioreactor
 condition (set temperature, pH)
 add inoculum
 allow to grow in batch phase (control pH, DO, temperature; sample at intervals)
 when nutrients exhausted, move to fed phase
 allow to grow in fed phase (control pH, DO, temperature; sample at intervals; supply additional nutrients)
 harvest product.

In particular, the computer system 10 may perform scaling according to two approaches: recipe scaling, in which whole processes are converted between scales, and instantaneous or time-point scaling, in which settings at a given point in time during a process are converted between scales.

Recipe Scaling

Figure 2:
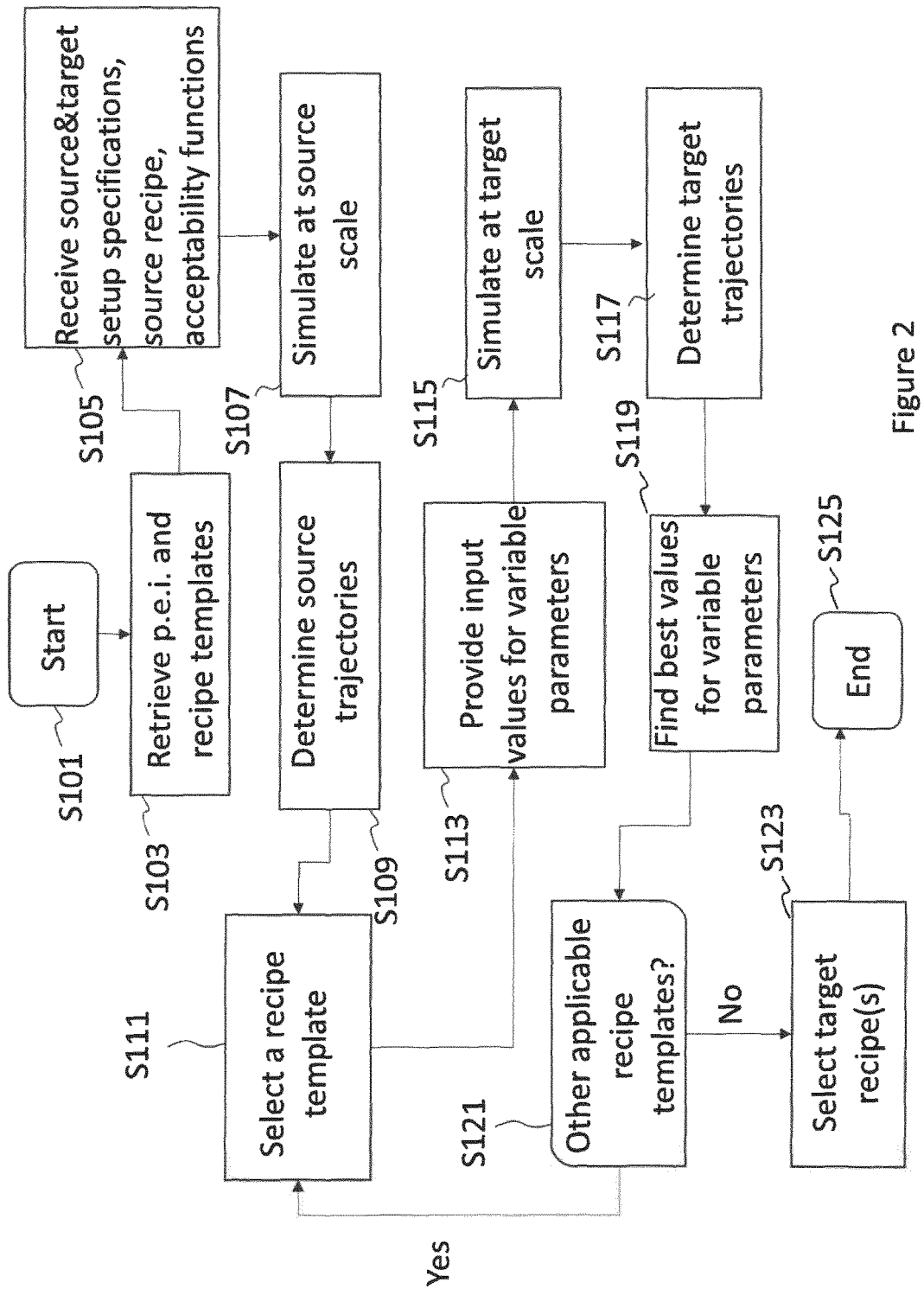
FIG. 2 shows a method for recipe scaling of a production process.
Figure 3:
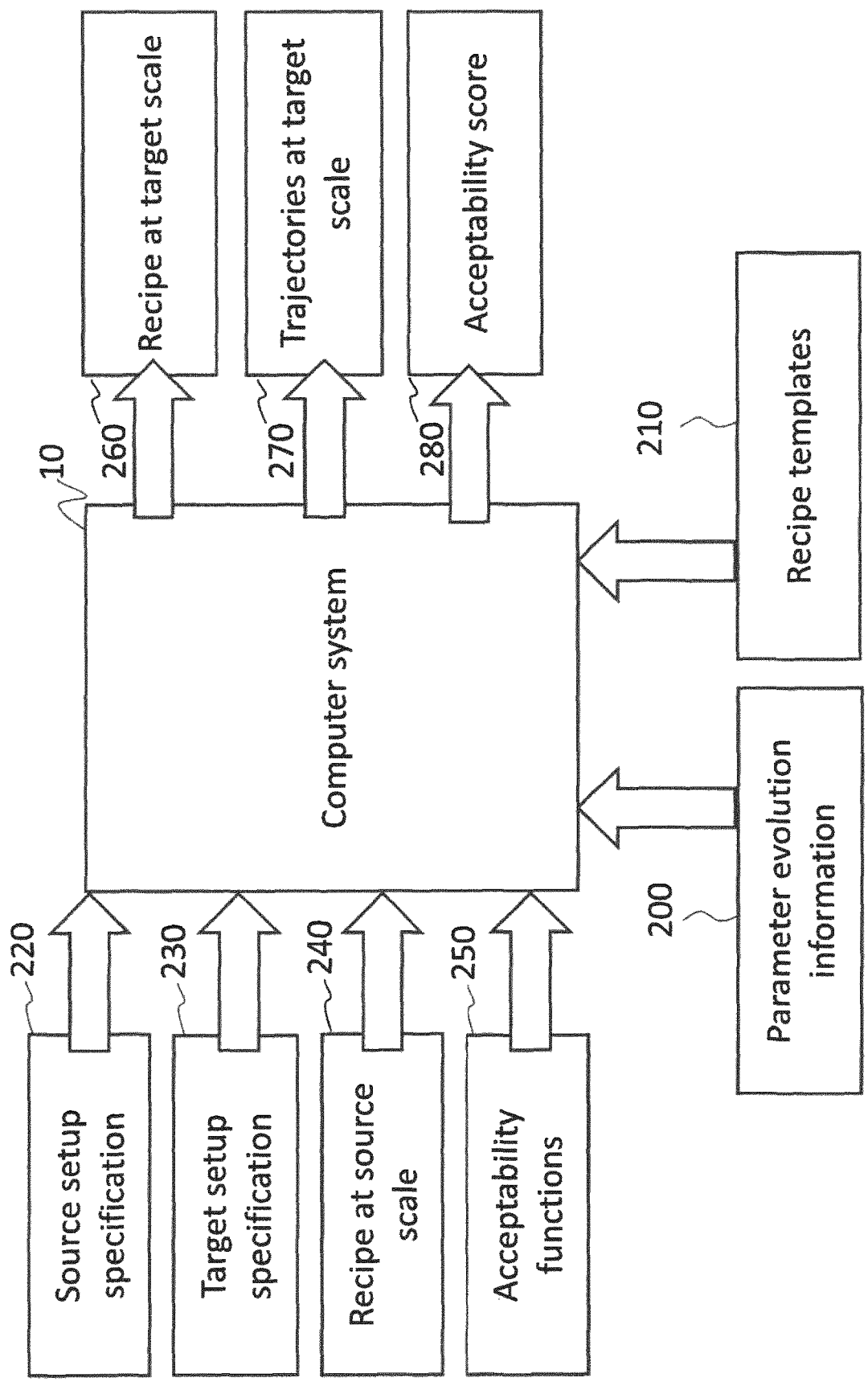
FIG. 3 shows a block diagram indicating inputs and outputs of the recipe scaling.

FIG. 2 shows an exemplary method for recipe scaling of a production process. The method will be described in conjunction with FIG. 3, which shows a block diagram indicating inputs and outputs of the recipe scaling.

A production process is defined by a plurality of steps specified by a plurality of process parameters, comprising recipe parameters and dynamic parameters. In the following, the method will be described for a production process in a bioreactor that is to be scaled from a source scale to a target scale.

Examples of recipe parameters include but are not limited to: stir speed (rpm), fill volume (L), total gassing rate (L/hr), gas percentage of O2(%), gas percentage of CO2(%) and parameters defining gassing profile, filling profile, temperature profile, inoculation and induction characteristics and sampling pattern. Profiles may be:
 constant rate (e.g. constant rate feed)
 exponential (e.g. feed exponentially increasing, which typically roughly corresponds to what the organism will be doing)
 polynomial (e.g. order 3 polynomial to correspond to a particular organism growth pattern);
and may be parameterised by one or more recipe parameters.

Examples of dynamic parameters include but are not limited to: tip speed (mps), mixing time (s), $k_La$ ($hr^{-1}$), power input (W), power input per volume ($Wm^{-3}$), Reynold's number, Froude number, minimum eddy size (μm), superficial gas velocity, cell density, cell metabolic state metric, carbon source availability, nitrogen source availability, secondary nitrogen source availability, inhibitor (toxin) concentration, pH, dissolved oxygen (%), dissolved CO2 (%).

Exemplary scenarios for a translation between scales may be the following. A small scale process is established at Ambr® 250 scale and the intention is to transfer the process as a single step to 50 L for production of larger quantities of product to evaluate downstream processing issues (e.g. purification/filtration). In another one, a manufacture process is established in organisation at a given large scale such as 50 L, and there is a need to scale down to e.g. Ambr® 15 or Ambr® 250 scale to perform initial clone selection; the scaled-down process needs to be "representative" otherwise the wrong clones will be selected and production when scaled back up to large scale will be compromised.

The method starts at S101 and the first step at S103 is retrieving parameter evolution information 200 and recipe templates 201. In the current implementation, by way of example, parameter evolution information is retrieved from a set of hard-coded formulae in the software, in conjunction with structured data in XML format stored on a file-system accessible to the software.

The parameter evolution information 200 characterises how the process parameters change with time, exemplarily including initial conditions for the process parameters and relations among process parameters. The parameter evolution information 200 describes physical modelling of the bioreactor in terms of parameters describing the bioreactor state (e.g. of fill volume) or the state of the production as determined by the bioreactor (e.g. power per volume), and biological modelling of the cell culture in the bioreactor (e.g. in terms of growth, oxygen consumption and pH depression).

In particular, the parameter evolution information 200 may comprise relations empirically derived from previous executions of the production process and equations derived by theoretical models about the evolution of the production process.

For example, the parameter evolution information 200 comprises experimental bioreactor data fittings, which are empirically derived mappings between recipe parameters (such as stirring speed, gassing rate and fill volume) and dynamic parameters (such as mixing time, $k_L a$ and power input). The experimental bioreactor data fittings link two or more process parameters to each other.

Additionally, the parameter evolution information comprises theoretically-derived equations and starting points both for a cell culture model and a bioreactor physical model. Examples of starting points for the cell culture model may be: growth rate 0.02 hr-1, temperature optimum 36 with growth reduced by 80% for each degree away, pH optimum 7.4 with growth reduced by 50% for each ¹/₁₀th of a unit away, specific 1C consumption rate scaled to a unit, growth rate saturating function of 1C source. In an alternative implementation, the cell culture model may be an empirical statistical model.

The bioreactor physical model may cover fill volume, temperature, analyte concentrations, pH, $k_L a$, mixing time, power input and dissolved oxygen. Details about each of these process parameters are provided in the following:

Fill Volume

The starting value for the fill volume is zero. Volume is accumulated due to liquid addition and bolus liquid addition, and reduced due to sampling. Evaporation is not considered in the following, but it may be, for example, by implementing a standard evaporation model whereby input gas is assumed to be devoid of water, and exit gas is assumed to be saturated (in the case with no condenser).

For a bolus addition of volume $v_b$, the fill volume is considered to update instantaneously, so that:

$$v_{new} = v_{old} + v_b$$

For the reduction of volume due to sampling, with a sample of volume $v_s$, the fill volume is considered to update instantaneously, so that:

$$v_{new} = v_{old} - v_s$$

During continuous liquid addition with a rate profile r(t), the fill volume updates according to the expression:

$$\frac{dv}{dt} = r(t)$$

Temperature

The temperature is driven by:
an external temperature, modelling a heating/cooling jacket or air stream;
temperature changes due to the supply of liquid.

Continuous changes to temperature depend on a single bioreactor-type parameter, indicating the rate of heat transfer between the external and internal temperature:

$$\frac{dT_{int}}{dt} = \frac{k_T}{V}(T_{ext}(t) - T_{int})$$

where $T_{int}$ is the liquid temperature, $k_T$ the heat transfer coefficient, and $T_{ext}(t)$ the external temperature.

The equations for temperature changes due to supply of liquid (either bolus supply or profiled supply) are analogous to those for analyte concentrations (see below).

Analyte Concentrations

Analyte concentrations change due to liquid addition and bolus liquid addition. For bolus liquid addition of volume $v_b$, for any given analyte at concentration $c_b$ in the bolus, the analyte concentration is considered to update instantaneously, so that:

$$c_{new} = \frac{v_{old} c_{old} + v_b c_b}{v_{old} + v_b}$$

where $v_{oid}$ is the volume prior to bolus liquid addition.

For continuous liquid addition with a rate profile r(t) with fill volume expressed as v(t), the concentration for any given analyte, c, at concentration $c_a$ in the supply liquid changes according to the following expression:

$$\frac{dc}{dt} = \frac{(c_b - c)}{v(t)} r(t)$$

pH

The following is a simplified model of buffering which aims at giving representative results without the need to specify the detailed buffering properties of media in detail. This is achieved by tracking both pH and buffering capacity as two distinct variables.

Liquid addition and bolus liquid addition both affect pH. Carbon dioxide mediated (or carbonic acid mediated) effects on pH are not yet considered, but there exist possible sets of theoretical equations for these in the literature which could potentially be included. The buffering capacity of the media is considered analogous to an analyte, so follows the evolution equations for analyte concentrations given above.

For bolus liquid addition of volume $v_b$ with pH $p_b$ and buffering capacity $b_b$ into medium with volume $v_m$, pH $p_m$ and buffering capacity $b_m$, the new medium pH is approximated as:

$$p_{m,new} = \frac{b_m p_{m,old} v_m + b_b p_b v_b}{b_m v_m + b_b v_b}$$

Dissolved Oxygen

Dissolved oxygen changes continually in the bioreactor due to the transfer of oxygen from the gas supply, as dictated by the $k_L a$; that is:

$$\frac{d[DO]}{dt} = k_L a(O^* - [DO])$$

where $O^*$ is the partial pressure of oxygen in the supply gas, relative to that in air.

The biological model for the cell culture aims at enabling the parsimonious description of a large range of bioprocesses salient for stirred bioreactor culture. The following model does not address, for example:

detailed metabolic aspects of the cells: these are relevant only inasmuch as they affect the behaviour of the cells in terms of interaction with the bioreactor or end product;

heterogeneity in the bioreactor: it is assumed that consideration of heterogeneity is adequately handled by penalising large mixing times in terms of utilities;

specifics and details of any individual process: the aim is to obtain broad but approximate coverage rather than a high degree of detail concerning a particular cell type or product, for example.

The biological model does instead focus on:

bioreactor-relevant culture effects, such as pH depression or elevation (which may trigger base or acid addition by the bioreactor system) and oxygen utilisation (which may affect gas flow or stir speed via the intermediary of a DO control loop);

end-product-relevant culture dynamics, such as modulation in cell activity or large-scale changes in cell metabolism e.g. to production and away from growth;

bioreactor-dependent culture effect, such as pH, DO or nutrient concentration effects.

The model is structured in terms of a number "culture model processes"; these are combined additively to produce a system of ordinary differential equations. Each culture model process has a number of constituent parts that govern its overall rate, multiplied by a maximum rate constant for that process. The constituent parts are functions of critical variables, and the output of these functions is combined multiplicatively.

For example, the rate may be determined as a function of temperature, T, and primary carbon source concentration, $c_{1C}$:

$$r = f_T(T) f_{[c1c]}(c_{1c})$$

The functions $f_T$ and $f_{[DO]}$ are selected from a (small) repertoire of biologically salient forms with a maximum of unity and minimum of zero. For example, temperature dependency might be described by $$f_T(T) = \exp\left(-\frac{(T-37)^2}{3}\right)$$

to indicate a temperature optimum at 37 degrees but with relatively small sensitivity to deviations from that temperature. Similarly, primary carbon source concentration dependency might be described by $$f_{c1c} = \frac{c_{1c}}{0.5 + c_{1c}}$$

to indicate a saturating maximum with half of the maximum rate achieved for a concentration of primary carbon source of 0.5 $gL^{-1}$.

This rate then determines the rate of change of a set of variables affected by the culture model process. For example, the rate may drive the growth of cell density, such that:

$$\frac{d\rho}{dt} = \rho \cdot r$$

The full expression for cell growth rate would then become:

$$\frac{d\rho}{dt} = r_g \cdot \exp\left(-\frac{(T-37)^2}{3}\right) \cdot \frac{c_{1c}}{0.5 + c_{1c}} \cdot \rho$$

In the above example, the culture model process has two dependencies (on primary carbon source and temperature) but only a single effect (on cell growth rate). A single culture model process may have multiple effects e.g. on cell growth rate and on primary carbon source consumption, which leads immediately to a system of equations.

$$\frac{d\rho}{dt} = r_g \cdot \exp\left(-\frac{(T-37)^2}{3}\right) \cdot \frac{c_{1c}}{0.5 + c_{1c}} \cdot \rho$$

$$\frac{dc_{1c}}{dt} = -r_c \cdot \exp\left(-\frac{(T-37)^2}{3}\right) \cdot \frac{c_{1c}}{0.5 + c_{1c}} \cdot \rho$$

A culture model process may depend, in terms of its rate, on one or more driving processes in a hierarchy. In this case, the rates of the driving process may be added (for example, consider when the driving processes relate to nutrient-dependent growth and production respectively, and the derived process is nutrient consumption), or multiplied. The specifics of the responses and the rates are covered in the following sections.

Culture Process Responses:

Temperature

A culture process (such as growth, production, or quiescence/death) may depend on media temperature. It is assumed that the process will be independent of external (jacket, driving) temperature, except inasmuch as this modulates the media temperature. It is anticipated that temperature dependence will typically comprise either a normal distribution, as described above, or, more usually, an asymmetric normal distribution i.e.

$$M(x) = \begin{cases} \exp\left(\frac{-(x-\mu)^2}{\sigma_r}\right) & x \geq \mu \\ \exp\left(\frac{-(x-\mu)^2}{\sigma_l}\right) & \text{otherwise} \end{cases}$$

For growth of Cho cells, for example, a normal distribution with $\mu=37$ and $\sigma=2$ would be a good starting point.

pH

A culture process (such as growth, production, or quiescence/death) may depend on media pH. It is anticipated that pH dependence will typically comprise a normal or asymmetric normal distribution.

For growth of Cho cells, for example, a normal distribution with $\mu=7.4$ and $\sigma=0.5$ would be a good starting point.

DO

A culture process (such as growth, production, or quiescence/death) may depend on dissolved oxygen saturation within the media. It is anticipated that DO dependence will reflect saturation or sigmoidal kinetics, i.e.

$$M(x) = \frac{x}{k+x}$$

or $$M(x) = \frac{1}{1 + \exp\left(-\left(\frac{x - k_{crit}}{k_{sens}}\right)\right)}$$

For growth of Cho cells, for example, saturation kinetics with $k_{crit}$=15% and $k_{sens}$=5% would be a good starting point.

Cell Metabolic State Response

The single metabolic state variable is used to summarise pertinent properties of the metabolic state of the cells. The meaning of this variable will be culture dependent, but it is primarily intended to summarise the cells' behaviour in terms of relative energetic commitment to growth and production. For example:
  metabolic state=−1 indicating commitment of 100% energy to growth
  metabolic state=1 indicating commitment of 100% energy to production.

Simulation starts with metabolic state set to zero and the state remains within the interval from −1 to 1 exclusive.

Clearly this is a vast simplification of the dynamics in real culture. However, it suffices to model the effect of induction and hence knock-on effects in terms of further amplification of the cell density (or otherwise).

The response of culture model processes related to production and growth are anticipated to take the form of a sigmoidal or reversed sigmoidal (i.e. one minus sigmoidal) respectively.

Cell Activity Response

The single cell activity state variable is used to summarise pertinent properties of cell activity, in particular quiescence or recovery from lag, whichever are applicable for the culture in question.

Simulation starts with cell activity set to zero, and the cell activity remains within the interval from −1 and 1 exclusive.

Where the culture exhibits a recovery component, it is anticipated that growth exhibits a sigmoidal response to the cell activity state variable, with other processes responsible for increasing the cell activity; in this case high cell activity state indicates that cells have largely recovered from, for example, defrosting.

Where the culture exhibits a death or quiescence component, it is anticipated that growth (and potentially also production) will exhibit a reverse sigmoidal response to the cell activity state variable, with other processes responsible for increasing the cell activity; in this case high cell activity state indicates a large number of quiescent or senescent cells.

Nutrient Responses

The interactions between cells and media are complex. Setting aside responses to pH, which have already been covered, the biological response to the media can be caricatured as:
  support of growth by the media e.g. due to the provision of adequate essential nutritive components, typically a sufficient carbon and nitrogen supply;
  support of production (of final product) by the media, with the same criteria;
  inhibition of growth by the media e.g. due to the presence of toxic media components;
  promotion of cell senescence or death by the media e.g. due to the presence of toxic media components;
  promotion of recovery from lag phase e.g. due to the presence of a supportive nutrient environment;
  promotion of transition from growth to production.

In many cases these drivers can be modelled as saturation kinetic or sigmoidal responses to concentrations of particular nutrients e.g.
  saturation kinetic response of growth to primary carbon source
  saturation kinetic response of growth to primary nitrogen source
  sigmoidal kinetic response of metabolic state change to inducer concentration
  either inverse sigmoidal or saturation kinetic response to toxic product or toxins.

In some cases, nutrient responses depend primarily on the ratio of two components of the media. This is particularly the case when multiple carbon sources are present, and one is utilised in preference to the other.

In this case, the cell culture process rate depends on a function (such as sigmoidal, saturation, or reverse sigmoidal) of the quotient of the concentrations of the components.

Culture Process Effects:

Growth Rate

Growth or death cell culture processes effect a change in the cell density, p:

$$\frac{d\rho}{dt} = r_q R \rho$$

where $r_g$ is the growth rate coefficient associated with the cell culture process, and its product with the rate of the cell culture process (i.e. R, from the cell process responses) indicates the specific growth rate. A constant non-zero R will therefore result in exponential growth (R>1), death (R<1) of the cell density.

The total change in cell density during culture simulation arises from growth and death due to pertinent cell culture processes, change to dilution (e.g. due to liquid bolus or profile liquid addition) and change due to supply of inoculum (i.e. due to the addition of a liquid with non-zero inoculum concentration).

pH Depression Rate

Cell culture processes may depress the media pH. The framework provides two means of modelling depression of pH.
  pH depression directly by a cell culture process
  pH depression indirectly due to the consumption or production of an acidic or basic media component due to a cell culture process.

In cases where the cell culture dynamics are considered at a high level (e.g. with an arbitrary carbon source) it is more appropriate to take the former approach.

In this case, pH is modulated according to the following expression:

$$\frac{d[pH]}{dt} = \frac{r_{[pH]} R \rho}{B}$$

where $r_{[pH]}$ is the pH depression coefficient for the cell culture process, R is the rate of the cell culture process at a given time, and B is the specific buffering capacity of the medium.

O2 Consumption Rate

Growth, maintenance and other metabolic cellular activities consume oxygen from the media. Cell culture processes that involve oxygen uptake modulate the media DO as follows:

$$\frac{d[DO]}{dt} = r_{[DO]} R\rho$$

where $r_{[DO]}$ is the DO uptake coefficient for the cell culture process and R is the rate of the cell culture process at a given time.

CO2 Production Rate

Similarly, metabolic activity, and in particular oxidative metabolism, produces carbon dioxide. Cell culture processes that involve carbon dioxide evolution modulate the media ppCO$_2$ as follows:

$$\frac{d[ppCO2]}{dt} = r_{[ppCO2]} R\rho$$

Cell Activity Modification Rate

As previously described, within the framework, cell activity state describes either cells moving out of a lag phase, or into quiescence/senescence. The cell activity state is a measure of the activity of the cells between −1 and 1 exclusive. To maintain the state within this interval, cell culture processes that modulate the state do so as follows:

$$\frac{d(\tanh(A))}{dt} = r_A$$

where A is the cell activity state, $r_A$ the cell culture process rate coefficient for cell activity state, and R is the rate of the cell culture process at a given time. No cell-density dependent effect is assumed, as the activity state is considered to apply homogeneously for all cells in the culture.

Cell Metabolic State Modification Rate

Cell metabolic state modification mirrors that for cell activity modification, that is:

$$\frac{d(\tanh(M))}{dt} = r_M R$$

where M is the cell metabolic state, $r_M$ the cell culture process rate coefficient for cell metabolic state, and R as above.

Nutrient Production Rates

A cell culture process may produce or consume components of the media. For example:
- cell growth and maintenance typically consume a carbon source and potentially a distinct nitrogen source;
- cell metabolism may produce product
- cell metabolism may produce toxic by-products.

Any given cell culture process may have zero or more nutrient production rate coefficients, each of which dictates that for the nutrient, i, in question:

$$\frac{dC_i}{dt} = r_{Ci} R\rho$$

where $r_{ci}$ is the rate coefficient.

Illustrative Culture Processes

The following illustrative culture process demonstrates many of the aspects of the framework described above.

| Cell culture process | Responses | Effects | Comment |
|---|---|---|---|
| Cell growth | Temperature: normal(37, 1) pH: normal(7, 0.5) dO: sigmoidal(10, 0.1) met. state: rev, sigmoidal(0.5, 5) act. state: rev, sigmoidal(0.5, 5) 1C source: saturation(0.1) | Growth rate: 0.5 pH depression rate: 1 o2 consumption rate: 5e3 1C source: −1 | Growth depends on correct temperature, pH, and adequate dO. It causes increase in cell count and depresses pH and oxygen. It also requires and consumes the primary carbon source. |
| Cell-death | Product: saturation(10) | act. state: 1 | Product causes cell death, modelled as a change in the cell activity state |
| Production | Temperature: normal(37, 1) pH: normal(7, 0.5) dO: sigmoidal(10, 0.1) met. state sigmoidal(0.5, 5) act state: rev. sigmoidal(0.5, 5) 1C source: saturation(0.1) | pH depression rate: 1 o2 consumption rate: 5e3 1C source: −1 Product: 1 | Complements growth depending on metabolic state. Does not increase cell count, but does increase product titre. |
| Induction | Inducer: saturation:0.001 | met. state: 1 | Presence of inducer causes cells to change metabolic state. |

Further, recipe templates 201 are retrieved at step S103. Recipes can be seen as a set of instructions dictating how the bioreactor behaves over time. Recipe templates are considered to be recipes with free or variable parameters. These variable parameters may result in very different recipes being produced from a given template (for example, if a path within a template is contingent on a free variable). Recipe templates may contain calculations based on the variable parameters, as well as on other process parameters within the process which they are running. Any of the recipe parameters listed above may be a variable parameter. For examples, profile parameters A, B and C for a feed rate profiled as A+B t+C t$^2$, wherein t is time, may be left free to vary.

A library of recipe templates 201 may be retrieved, wherein different recipe templates may comprise different steps or instructions and/or may have different variable parameters.

Recipe templates 201 may comprise marks identifying phases of the production process, which are used together with acceptability functions, as explained below.

The acceptability functions 250 are received at step S105. In the exemplary implementation, the software supplies a user interface by which acceptability functions can be selected from a library and then parameterised, or designed graphically. The library in this case provides acceptability functions indicating, amongst others, (a) a range (b) a single point (c) a normal distribution. For further examples see the canonical forms below. The acceptability functions define conditions for the values of the process parameter(s) at the source scale and/or at the target scale, in particular they define how acceptable these values are, when taken alone or in relation to one another. The value for acceptability may be a real number between 0 and 1, boundaries included.

There may be absolute and relative acceptability functions.

An absolute acceptability function maps from one or more process parameters at the same scale to an evaluation. Examples of absolute acceptability functions define conditions for the following parameters:

Reynolds number (Rn): 0 for low Rn, increasing to 1 as Rn moves into turbulent zone, then 1 afterwards;

$k_L a$: 0 for low $k_L a$, increasing as saturating function to 1 as $k_L a$ increases;

mixing time: 1 for low mixing time, and then when mixing time exceeds 20 s, equal to 20 s/mixing time (i.e. decreasing towards 0);

superficial gas velocity (SGV): 1 for low SGV, with sigmoidal decline with increasing SGV for larger SGV, towards 0, to reflect increased risk of foam with increasing SGV;

power per volume: normal distribution around some maximum;

stir speed: 0 for 0 . . . 5% and for 95 . . . 100% of bioreactor stir speed, 1 otherwise (preferable to run with the system not at its limits); or linear increase from 0 at 0% to 1 at 5%, then flat until 95%, then linear decrease to 0 at 100%;

eddy size: 1 for eddy size greater than 5× organism size, then linearly to 0 for 2× organism size, to reflect increasing risk to organism as eddy size decreases;

product concentration at harvest time: 0 for 0, with saturating increase (tends to 1 as product concentration tends to infinity) as titre increases;

DO: 0 for 0 . . . 10%, then a sigmoidal curve between 10% and 20% up to 1, and then 1 for >20% to ensure adequate oxygen for organism in sensitive region;

SGV+protein concentration: 1 for low SGV or low protein concentration, decreasing to 0 as either become large; similarly stir speed+SGV could also affect risk of foaming;

power per volume+cell density: normal distribution around some optimum, but optimum shifts from low to large power per volume as cell density increases (reflecting protective effect of cells on other cells);

product concentration+product quality: 0 if either are 0, then increasing as proportional to the product of concentration and quality.

A relative acceptability function maps from a combination of (one or more) process parameters at the source scale and corresponding (one or more) process parameters at the target scale to an evaluation. For example, a way of combining two corresponding process parameters at different scales is to compute their difference or relative difference, i.e. absolute value of (value in source−value in target)/(maximum (value in source, value in target)). Examples of relative acceptability functions define the following conditions:

0 if mixing time is less at source scale than at target scale, otherwise 1 (ensures no loss of mixing when moving up scales);

normal distribution of PPV around a delta of 0 (ensures PPV a typical parameter for matching is conserved between scales);

1 for $k_L a$ greater at target than source scale, otherwise sigmoidal decrease to 0 as $k_L a$ differs increasingly;

normal distribution around 0, standard deviation of 0.2 for cell density (ensures growth curves conserved between source and target).

Generally, the acceptability functions may be one-dimensional, two-dimensional or with higher dimensions. Some examples for canonical forms for one-dimensional and two-dimensional acceptability functions are reported below.

A one dimensional acceptability function can take one of the following canonical forms:

zero throughout, except at a given exact value, at which it is one (this expresses a need to restrict the solution space to a precise value, for example, if a particular fill volume is needed at the small scale);

a normal distribution (this expresses the idea that a parameter value such as $k_L a$ has an optimum, but with some room for manoeuvre around this); one within a range, zero outside that range (this expresses the idea that a parameter value should remain within this range, e.g. that mixing time should be less than a given maximum)

A two dimensional acceptability function can take one of the following canonical forms:

$f(x,y)=0$ unless $x=y$, in which case $f(x,y)=1$ (this expresses the need to find an exact match between scales e.g. for power input per volume);

$f(x,y)=0$ unless $x \geq y$, in which case $f(x,y)=1$ (this expresses the need to restrict solution space to the situation where, at the target scale, the parameter value exceeds that at the source, for example in terms of oxygen transfer)

$f(x,y)=0$ unless $x \leq y$, in which case $f(x,y)=1$ (this expresses the need to restrict solution space to the situation where, at the target scale, the parameter value is less than that at the source, for example in terms of mixing time)

$f(x,y)=N(x-y; m, s)$ (this expresses a benefit from having as close possible but not necessarily a perfect match between the scales e.g. for power per volume)

$f(x,y)=N((x-y)/\max(x,y); m, s)$ (as above, but ratiometric).

In the recipe scaling case, acceptability functions may be attached to specified parts of process templates. For example, a process template might specify "start of batch" and "end of batch", and an acceptability function would then be attached to the interval between these two waypoints, and considered to apply only for those parts of the process. For example, in batch phase, only those acceptability functions may be applied that do not set the acceptability value to depend on cell density, because in batch phase there may be some variability as the cells grow up to use their nutrients up. Conversely, in fed phase, only those acceptability functions may be applied for which the acceptability value depends on cell density, because by start of fed phase, variability due to initial inoculum should have been "evened out" because they were all provided with same amount of nutrient in batch phase. In another example, those acceptability functions for which the acceptability value depends product titre (concentration) may be applied only in harvest phase, because titre is not relevant before the harvest point.

At step S105 also source setup specification 220 and target setup specification 230 are received. In the exemplary implementation, the user selects a source and target setup from a list. The software retrieves information concerning a given source or target setup, including the permitted configurations, minimum stir speed, maximum stir speed, mixing properties, and so on, from structured data in an XML file, which is stored on the filesystem in a place accessible to the software.

The setup specifications are description of the scales, namely of the equipment at source scale and target scale, specifying e.g. volumes and number/type of equipment components. A source setup specification 220 may e.g. be Ambr® 250 with mammalian impeller and a target setup specification 230 may e.g. be any of 2 L UniVessel, 50 L STR with 3+6 impeller and combi sparger, 2000 L STR with 3+6 impeller and combi sparger.

Further, at step S105, also a recipe 240 for the source scale is received. In the exemplary implementation, the software provides a user interface by which the user can design a recipe or recipe template by successively adding and removing steps, and by parameterising steps. The software persists the recipe templates in an XML-based repository using the Microsoft .net serialiser to persist the object model for the recipes represented internally as objects within the software implementation.

An example for the source recipe 240 may correspond to the following procedure: "Fill bioreactor with 0.2 L of given media, heat to 35 degrees, inoculate with clone to a density of 1e6 cells mL-1, incubate stirring at 600 rpm for 36 hrs controlling pH to 7.4 with bottom and top control i.e. addition of acid or base as needed to push pH back to 7.4; maintain temperature; gas at a rate of 0.1 of total volume per minute with air; feed with complex feed for 36 hrs continuing to monitor and control pH, temperature; control DO with stirring and gassing, add inducer to trigger production. Harvest after 36 hrs."

Then at step S107 the execution of the production process is simulated at the source scale using a combination of the source setup specification 220, the source recipe 240 and the parameter evolution information 200. The source setup specification 220 provides a sort of framework for the simulation, while the source recipe 240 and the parameter evolution information 200 define how the process develops.

The physical, chemical and/or biological aspects of the production process are simulated. In particular, the process simulation comprises purely physical modelling (e.g. of fill volume), bioreactor modelling derived from physical characterisation of bioreactors (e.g. mapping from fill volume and stir speed to power per volume), and biological modelling of the organism (in terms of growth, oxygen consumption and pH depression).

Figure 6:
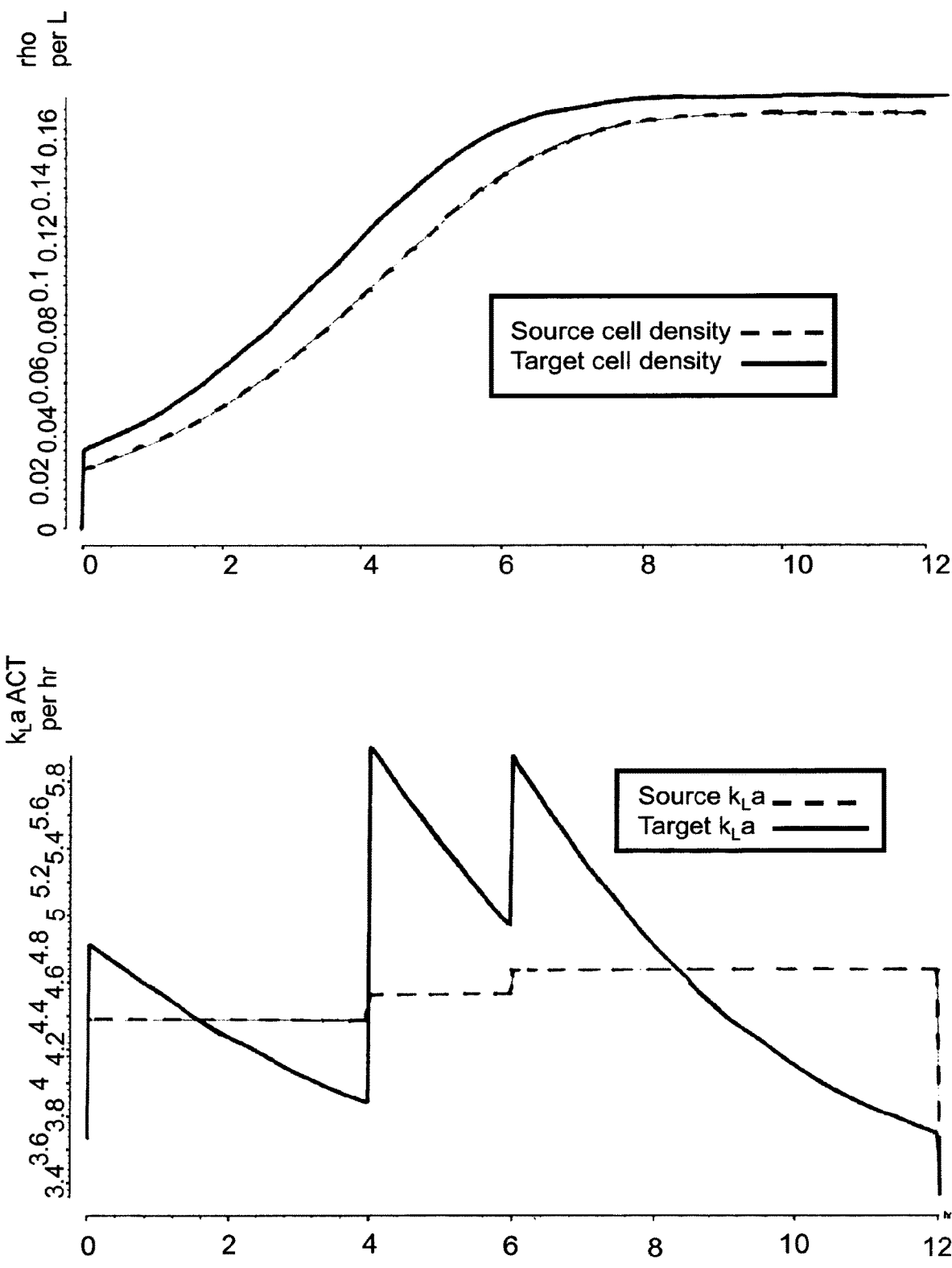
FIG. 6 shows exemplary target trajectories.

From the simulation at source scale, source trajectories for the process parameters are determined at S109. This means that the values of the process parameters are recorded at different times during the simulation, so that a time dependence of the process parameters can be determined. The data points may be fitted to obtain fitting functions for the time evolution of the parameters. FIG. 6 shows examples of trajectories, which will be discussed below.

Afterwards, at steps S111 and S113, a tentative target recipe is chosen. A recipe template is selected among the plurality of recipe templates 210 and some input values are provided for the variable parameters in the selected recipe template. The combination of the selected recipe template and the provided input values provides a tentative target recipe that can be used at step S115 for simulating the production process at the target scale, similarly to step S107.

Figure 4:
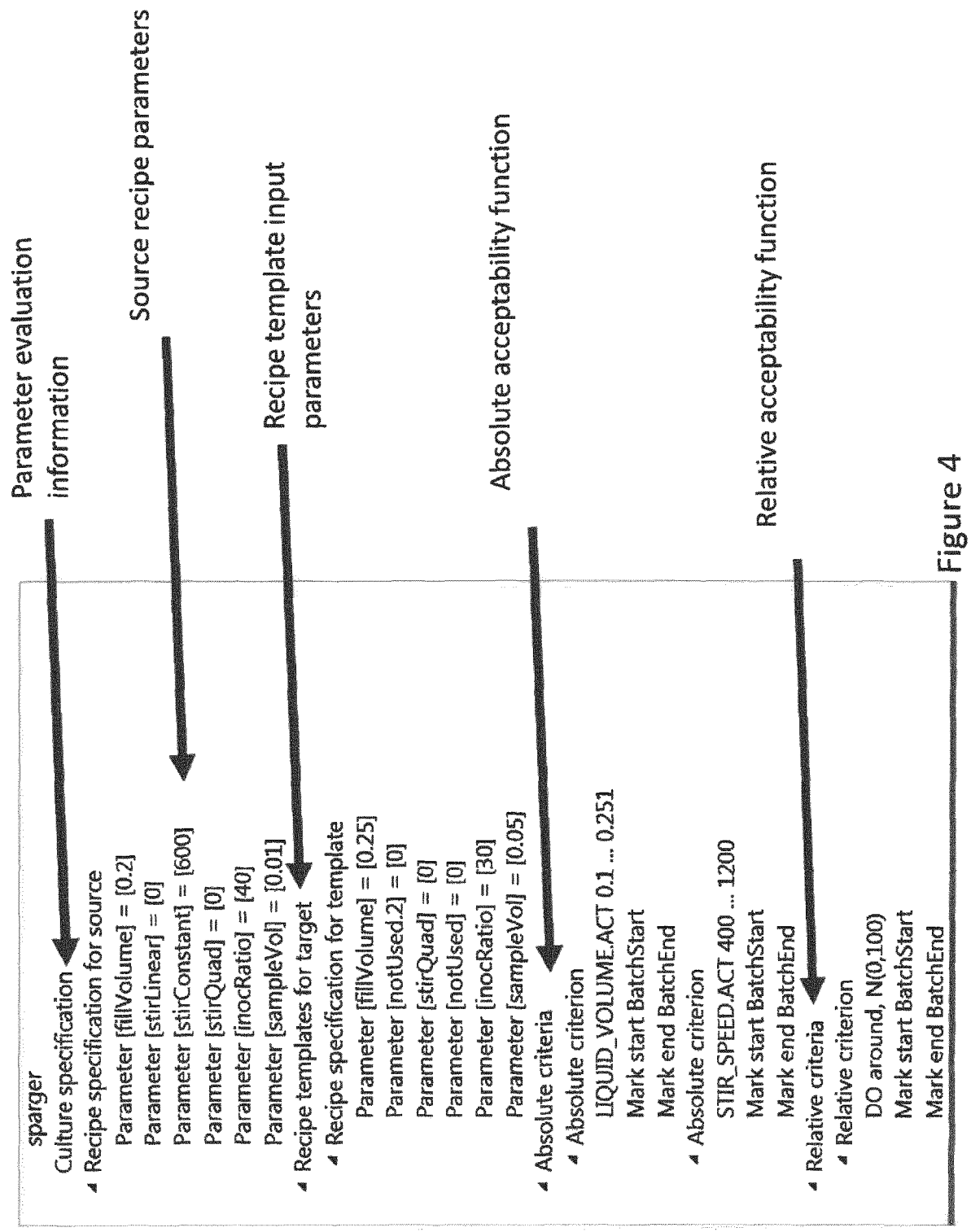
FIG. 4 shows part of an exemplary input for recipe scaling.

FIG. 4 shows part of an exemplary input for recipe scaling, in which parameter evolution information 200, source recipe 240, input values for a selected recipe template 210 and acceptability functions 250 are visible, while the source and target setup specifications are not shown.

Further, at step S117, target trajectories 270 corresponding to the time evolution of process parameters at the target scale are determined, exactly as for the source trajectories.

Then at step S119 the initial guess for the variable parameters provided by the input values is modified to "best" satisfy the conditions given by the acceptability functions 250. In particular, the simulation may be run multiple times to explore the space available for the variable parameter(s), until preferred points or surfaces in the space are found, i.e. the ones that make the target trajectories 270 most compliant with the acceptability functions 250. The compliance of the target trajectories 270 with the acceptability functions 250 is indicated by an acceptability score 280. Different degrees of compliance may be of interest, such as considering only the values of the variable parameter that maximise the acceptability score 280 or considering also a plurality of values that yield an acceptability score 280 above a certain threshold. The plurality of values may form a single (possibly multi-dimensional) range or non-adjacent ranges.

At step S121 it is checked whether there are other applicable recipe templates that could be used as basis for a target recipe and, if so, steps S111-S115 are repeated.

Finally, at S123, one or more target recipes 260 are selected among the tested tentative target recipes, i.e. the recipe templates with corresponding values for the variable parameters. The selection is based on the acceptability score 280 and may be such that only the tentative target recipe with the highest acceptability score 280 is considered or more tentative target recipes with an acceptability score 280 above a certain threshold are considered.

The method ends at S125.

Figure 5:
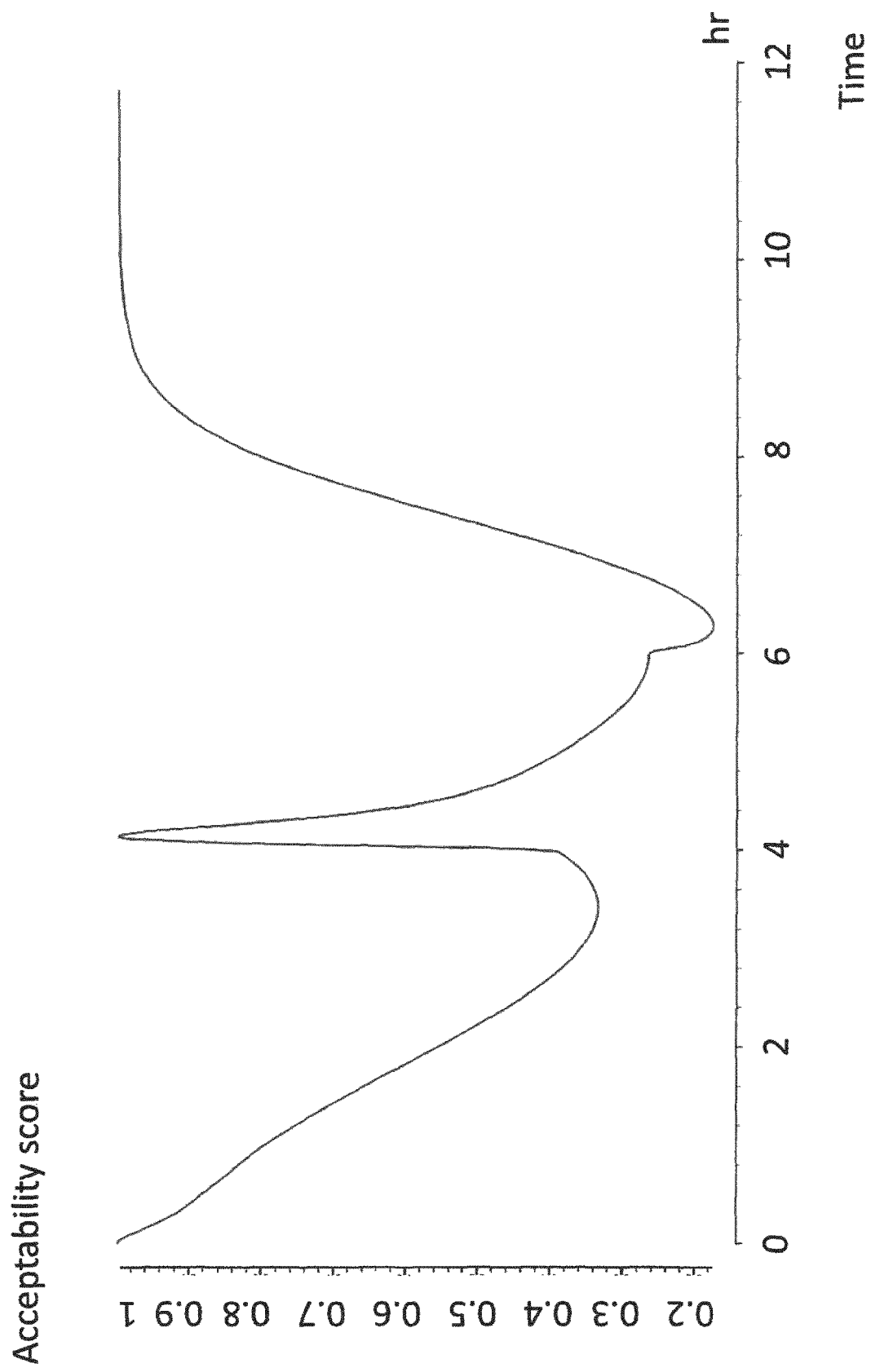
FIG. 5 shows an acceptability score as a function of time.

In some cases, the target recipe(s) 260 may be output, e.g. as a file. An example for an output indicating the target recipe 260 may be: "on the ambr 250, use recipe template named "ramp stir speed", with the initial inoculum set to 0.2% of the total volume and DO controlled to 35% throughout". The acceptability score 280 may also be output, e.g. as text "this will give a score of 80% of the optimal translation from your 50 L recipe" or as a plot in function of time, as shown in FIG. 5. Further, the simulated target trajectories 270 may be output e.g. as plots.

FIG. 5 shows an acceptability score as a function of time and FIG. 6 shows exemplary target trajectories.

It can be seen that the acceptability score 280 in FIG. 5 has two troughs around the 4th hour and the 6th hour. The advantage of outputting the target trajectories 270 is that causes for the poor performance in these phases may be readily identified. For example, considering the target trajectories in the upper part of FIG. 6 for the cell density, it is apparent that the cell density evolves similarly at the source scale and at the target scale. Since one of the objectives is to maximise the similarity between the processes at different scale, the cell density will have scored high. Instead, the target trajectories in the lower part of FIG. 6 for $k_La$ show that the evolution of $k_La$ at the target scale is not similar to the one at the source scale. Accordingly, $k_La$ may be at least partly the cause for the troughs in the overall acceptability score 280.

To summarize, the method involves the mapping of a recipe at one scale onto a recipe at a second scale subject to some constraints by means of evaluating the trajectories that result from the simulation of the recipes at each of the scales in question. In particular, trajectories that match best according to the acceptability functions are used to infer values for appropriately populating a recipe template.

The method can be generalised to a train scaling involving an arbitrary number of scales, i.e. a translation that starts from a source scale and arrives at a final target scale by passing through and translating for each of a plurality of intermediate target scales.

When applying the recipe scaling method of FIG. 2, setup specifications for the intermediate target scale(s) are received at S105 and the acceptability functions 250 cover all scales, i.e. define conditions across all scales. In addition, steps S113, S115 and S117 must be performed also for each intermediate target scale. Further, step S119 involves a simultaneous search for "best" values (optimal values or ranges) for all target scales, i.e. the one or more intermediate target scale and the final target scale.

An exemplary scenario for a train scaling may be going from Ambr® 15 to UniVessel® 2 L to STR® 50 L to SIR® 1000 L to STR® 2000 L. In particular, each of these scales may belong to a scale group as follows:

Configuration 1: Ambr® 250, attached to small scale group
Configuration 2: UniVessel® 2 L, attached to small scale and intermediate scale group
Configuration 3: STR® 50, attached to intermediate scale and large scale group
Configuration 4: STR® 1000, attached to large scale group
Configuration 5: SIR® 2000, attached to large scale group.

The following acceptability functions 250 are defined for the groups:
1) Small Scale Group:
relative acceptability function: normal function of delta in $k_La$ with mean 0, standard deviation 1 $hr^{-1}$;
relative acceptability function: normal function of delta in PPV with mean 0, standard deviation 0.2 $Wm^{-3}$;
absolute acceptability function: 0 valued when between 0 and 5% and 95% and 100%, 1 otherwise (concerns the stir speed of bioreactor as % of maximum);
absolute acceptability function: sigmoidal function with value 0 for 0, a sharp rise around 20 up to 1, for dissolved oxygen.
2) Intermediate Scale Group:
relative acceptability function: normal function of delta in PPV with mean 0, standard deviation 0.1 $Wm^{-3}$
3) Large Scale Group:
relative acceptability function: normal function of delta in PPV with mean 0, standard deviation 0.1 $Wm^{-3}$
absolute acceptability function: 1 kW/(1 kW+power input)

It can be seen that, in the train scaling, particularly, the acceptability functions 250 link the different scales so that the process is scaled for each scale taking into account also the requirements that will arise for following scales.

A train scaling may be computationally expensive, however the acceptability functions can be used when exploring the space of the variable parameters.

By way of example, a simple case with 3 target scales, A, B and C can be considered. A and B are linked by an acceptability function that drops below 0.5 if the $k_La$ differs by more than 1 $hr^{-1}$, while an acceptability function linking B and C is such that if the $k_La$ between B and C differs at all, it drops to 0, otherwise it is 1. The variable parameter is the stir speed, so the stir speed for scale A, the stir speed for scale B, and the stir speed for scale C need an input value. A threshold of 0.5 is set for the final acceptability score, and the acceptability score functions are combined by considering the product of the acceptability scores.

After an input value for the stir speed at scale A is chosen and an input value for the stir speed at scale B is chosen, $k_La$ can be computed based on the stir speed values and, in particular, the $k_La$ difference between A and B. There will only be certain regions for which the $k_La$ differs by less than 1 $hr^{-1}$ and, thus, the acceptability score is greater than 0.5. Since acceptability scores are by definition all lower or equal to 1, and since the acceptability score functions are combined as a product, it can already be inferred that any values for B that are not in the above-mentioned region will result in a final acceptability score lower than the threshold. Accordingly, a range of feasible input values for B is given on the basis of the input value for A.

In turn, having proposed a candidate stir speed for scale B, this can be immediately propagated to scale C, because only that stir speed which gives identical $k_La$ at scale C is acceptable (using the same logic as before).

The conclusion is that the optimisation should be mainly performed over the value for A, and that the range for the B value for optimisation is diminished as a function of the candidate stir speed for A, and that there is no need to optimise over C because it arises automatically from B. This gives the appropriate set of clues to the optimiser to enable it to move rapidly to a solution, rather than exploring all possible values for stir speed at A, B and C.

Time-Point Scaling

Figure 7:
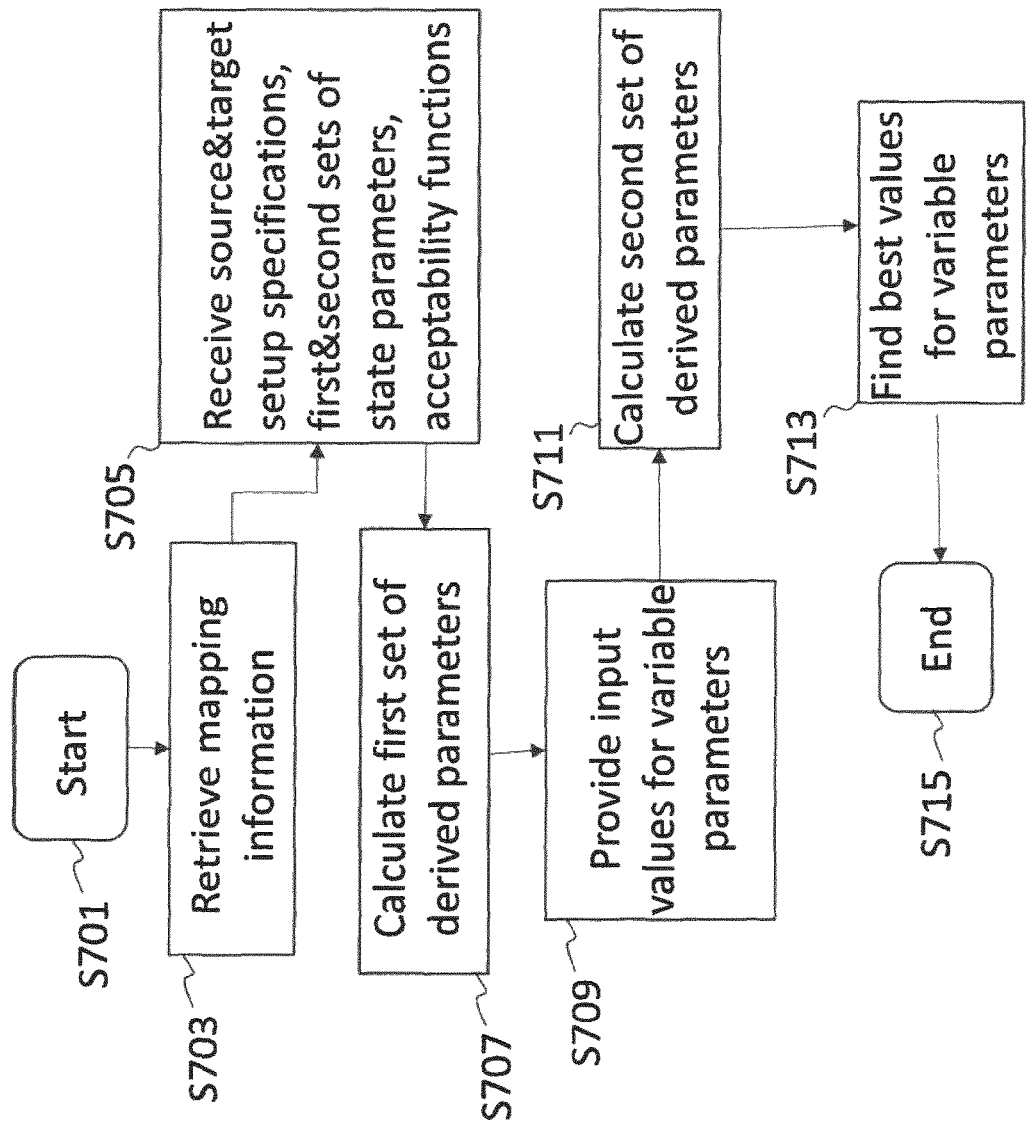
FIG. 7 shows a method for time-point scaling of a state of a production equipment.
Figure 8:
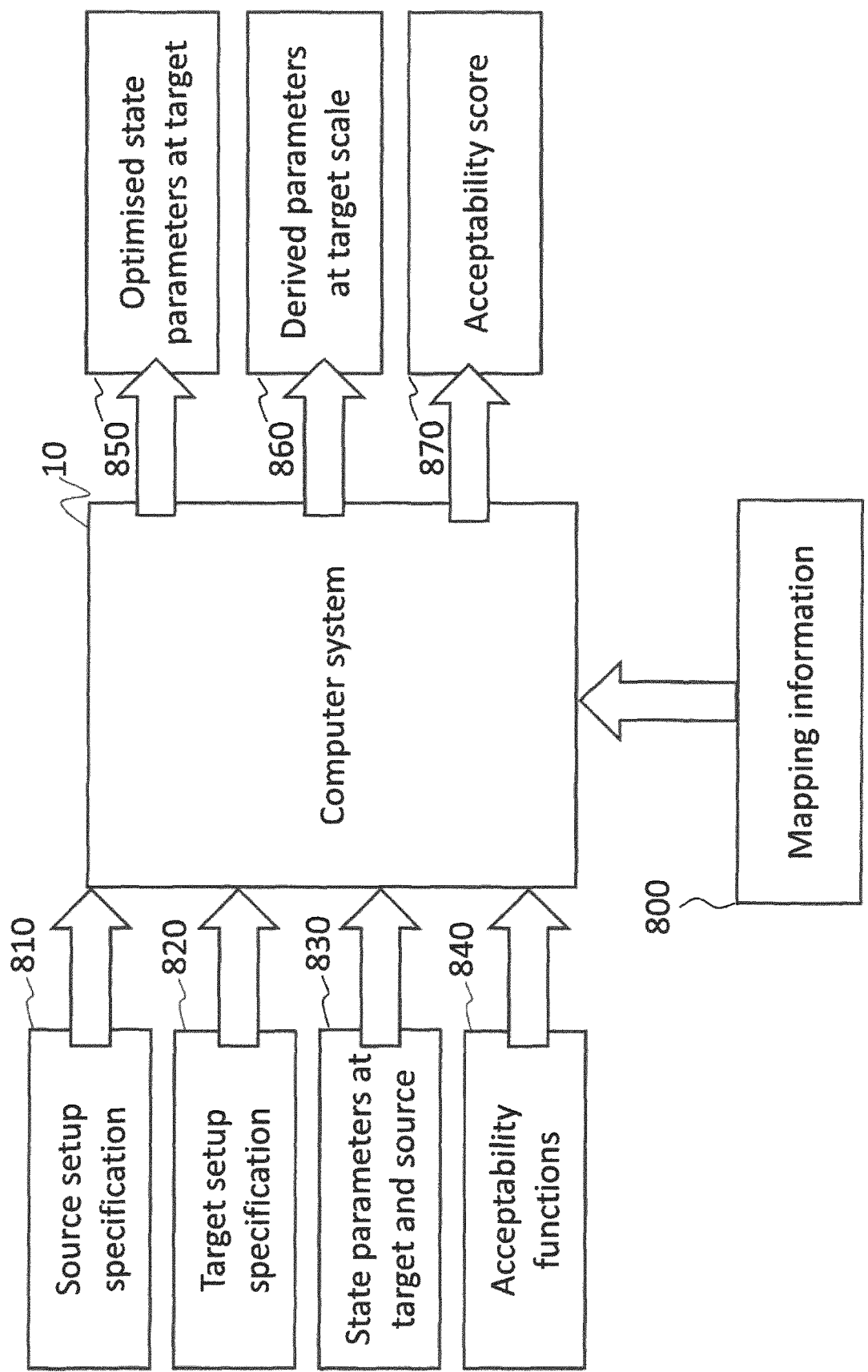
FIG. 8 shows a block diagram indicating inputs and outputs of the time-point scaling.

FIG. 7 shows an exemplary method for time-point scaling of a state of a production equipment. The method will be described in conjunction with FIG. 8, which shows a block diagram indicating inputs and outputs of the time-point scaling.

In the following, the method will be described for a production equipment including a bioreactor that may be used to perform any of the production processes discussed with reference to the recipe scaling.

Examples of bioreactor configurations include but are not limited to: Ambr® 15 fermentation, Ambr® 15 cell culture, Ambr® 250 mammalian, Ambr® 250 microbial, UniVessel® 2 L, STR® 50 with ring sparger and 2×3 blade impellers, STR® 200 with micro sparger and 3+6 blade impellers, and SIR® 1000 with ring sparger and 2×3 blade impellers.

The state of a production equipment is defined by state parameters, which may include but are not limited to: stir speed (rpm), fill volume (L), total gassing rate (L $hr^{-1}$), gas percentage of O2(%) and gas percentage of CO2(%).

The method starts at S701 and the first step at S703 is retrieving mapping information 800. In the exemplary implementation, mapping information is stored alongside bioreactor configuration in an XML file which is accessible to the software.

The mapping information 800 characterises how the state parameters relate to derived parameters, which characterise a given point in time during the production process. The derived parameters include but are not limited to: tip speed (mps), $k_La$ ($hr^{-1}$), mixing time (s), power input (W), power input per volume (W/$m^3$), Reynold's number, Froude number, minimum eddy size (μm) and superficial gas velocity.

In particular, the mapping information 800 may comprise experimental bioreactor data fittings derived from previous executions of the production process and/or equations derived by theoretical models.

The mapping information 800 may comprise different relations between state parameters and derived parameters that apply to different production equipment. Accordingly, in the retrieving step S703, only the relations appropriate for the case at hand may be retrieved.

For example, the time-point scaling may be applied between an Ambr® 250 bioreactor and a UniVessel® 2 L bioreactor. The retrieved mapping information 800 may include a mapping from stir speed, fill volume and gassing rate onto $k_La$ and PPV, as well as the equation linking stir speed and tip speed for a given geometry of the bioreactor.

At step S705, source setup specification 810, target setup specification 820 and acceptability functions 840 are received. In the exemplary implementation, source set up and target set up are specified through the user interface by the user, selecting from a combobox. The details of the source and target setup, in terms of the associated parameters and mapping, are stored in an XML file on the filesystem to which the software has access.

The setup specifications are description of the scales, namely of the equipment at source scale and target scale, specifying e.g. volumes and number/type of equipment components. Continuing the example from above, the source setup specification 810 may be Ambr® 250 and a target setup specification 840 may be UniVessel® 2 L.

The acceptability functions 840 may have any of the canonical forms illustrated previously. For the above example, three acceptability functions 840 may be received: a relative acceptability function being a normal distribution with mean 0 $hr^{-1}$ and standard deviation 1 $hr^{-1}$ for the difference between $k_L a$ at the source scale and at the target scale; a relative acceptability function being a normal distribution with mean 0 s and standard deviation 5 s for the difference between mixing time at the source scale and at the target scale and an absolute acceptability function requiring the tip speed at the target scale to be 5% of the maximum in the bioreactor (i.e. 0 for tip speed lower than 5% and 1 for tip speed higher than 5%).

At step S705, also a first set of state parameters at the source scale and a second set of state parameters at the target scale 830 is received. The first set of state parameters for the above example may be: stir speed 400 rpm, gassing rate 0.02 L $min^{-1}$, fill volume 0.2 L, gas 100% air. The second set of state parameters may be: fill volume 2 L, gassing rate 0.2 L $min^{-1}$, gas 100% air, with the stir speed left as variable parameter, which will be populated later.

Figure 9:
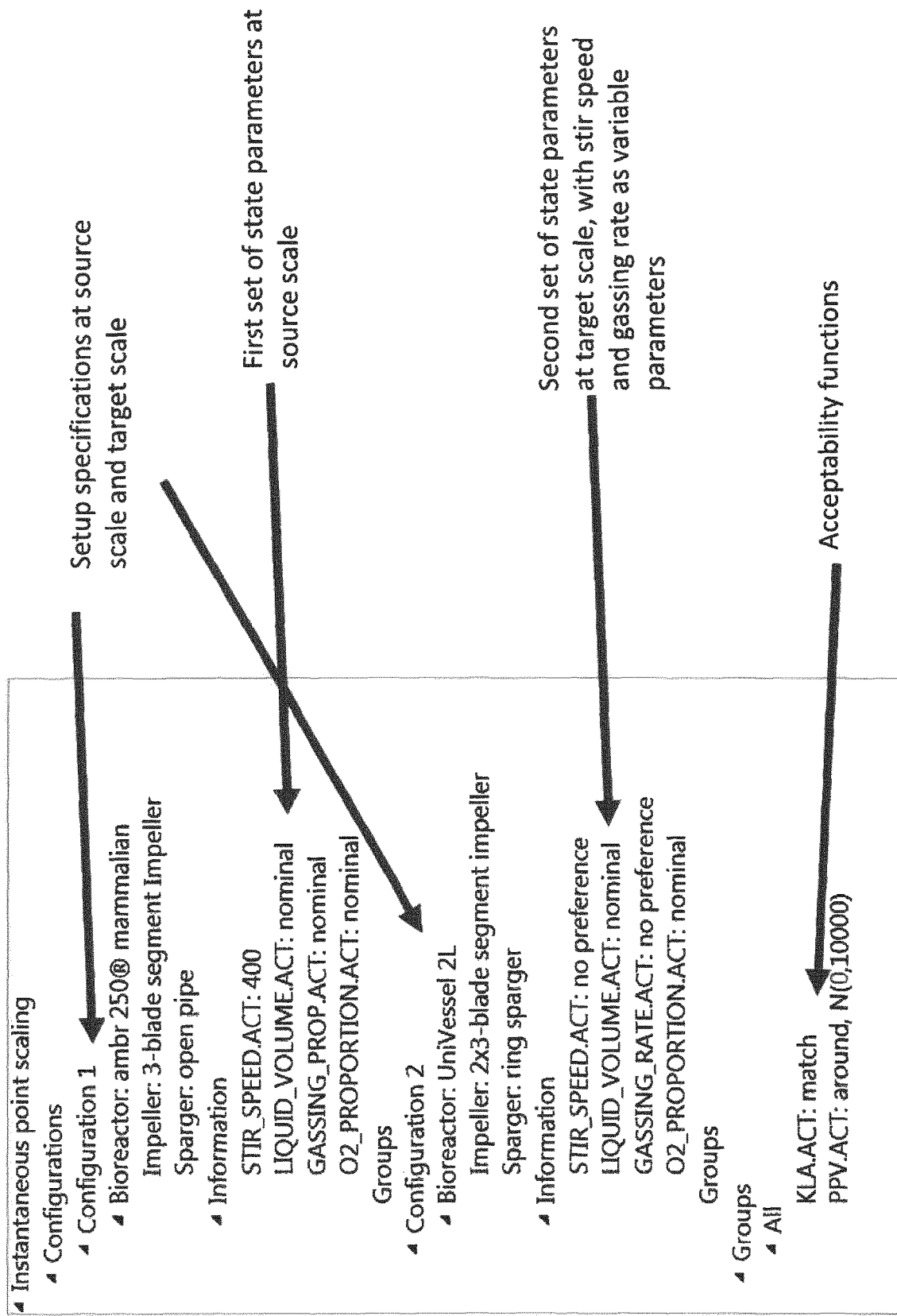
FIG. 9 shows part of an exemplary input for time-point scaling.

FIG. 9 shows part of an exemplary input for time-point scaling, in which source and target setup specifications 810 and 820, first and second sets of state parameters 830, and acceptability functions 840 are visible, while mapping information 800 is not shown.

Then at step S707 a first set of derived parameters for the source scale is calculated. In the given example, $k_L a$ and mixing time are computed at the ambr 250 scale, given stir speed 400 rpm, gassing rate 0.02 L $min^{-1}$, fill volume 0.2 L and gas 100% air and using the retrieved mapping information 800.

Then at step S709 input value(s) for the variable parameter(s) are chosen. For example, the input value for the stir speed at the target scale may be 40 rpm, which is the midpoint of the minimum and the maximum stir speed for the UniVessel 2 L. Using the input value(s), at step S711 a second set of derived parameters 860 for the target scale is calculated, similarly to step S707. Accordingly, in the given example, $k_L a$ and mixing time are computed at the UniVessel® 2 L scale, given stir speed 40 rpm, gassing rate 0.2 L $min^{-1}$, fill volume 2 L and gas 100% air and using the retrieved mapping information 800. Further, the tip speed is computed according to the mapping information 800 from properties of the UniVessel® 2 L scale geometry and the candidate stir speed 40 rpm.

Then at step S713 the initial guess for the variable parameters provided by the input values is modified to "best" satisfy the conditions given by the acceptability functions 840. In particular, the space available for the variable parameter(s) is explored, until preferred points or surfaces in the space are found, i.e. the ones that make the second set of state parameters most compliant with the acceptability functions 840.

The compliance of the state parameters at the target scale with the acceptability functions 840 is indicated by an acceptability score 870. Different degrees of compliance may be of interest, such as considering only the values of the variable parameter that maximise the acceptability score 870 or considering also a plurality of values that yield an acceptability score 870 above a certain threshold. The plurality of values may form a single (possibly multi-dimensional) range or non-adjacent ranges. If each acceptability function 840 gives a partial acceptability score, the total acceptability score may be given by the product or the mean or other combinations of all partial acceptability scores.

The result is an optimised second set of state parameters 850 for the target scale.

In the given example, each time a new input value from the space of the stir speed is chosen, $k_L a$, mixing time and tip speed are derived again and the corresponding acceptability score is computed. The final result is, thus, an optimised stir speed or an acceptable range for the stir speed at the UniVessel 2 L scale.

The method ends at S715.

The method can be generalised to a train scaling involving an arbitrary number of scales, i.e. a translation that starts from a source scale and arrives at a final target scale by passing through and translating for each of a plurality of intermediate target scales.

When applying the time-point scaling method of FIG. 7, setup specifications for the intermediate target scale(s) are received at S705 and the acceptability functions 840 cover all scales, i.e. define conditions across all scales. In addition, steps S709 and S711 must be performed also for each intermediate target scale. Further, step S713 involves a simultaneous search for "best" values (optimal values or ranges) for all target scales, i.e. the one or more intermediate target scale and the final target scale.

The invention claimed is:

1. A computer-implemented method of scaling a production process to produce a chemical, pharmaceutical and/or biotechnological product, the scaling being from a source scale to a target scale, wherein the production process is defined by a plurality of steps specified by one or more process parameters controlling an execution of the production process, the method comprising:

retrieving:
  parameter evolution information that describes the time evolution of the process parameter(s);
  a plurality of recipe templates, wherein:
    a recipe comprises the plurality of steps defining the production process, and
    a recipe template is a recipe in which at least one of the process parameters specifying the plurality of steps is a parameter being variable and having no predetermined value at the outset;

receiving:
  a source setup specification of a source setup to be used for executing the production process at the source scale, the source setup specification comprising the source scale value;
  a target setup specification of a target setup to be used for executing the production process at the target scale, the target setup specification comprising the target scale value;
  a source recipe defining the production process at the source scale;
  at least one acceptability function defining conditions for the values of the process parameter(s) at the source scale and/or at the target scale;

simulating the execution of the production process at the source scale using the source setup specification, the source recipe and the parameter evolution information;

determining, from the simulation, one or more source trajectories for the process parameter(s), wherein a trajectory corresponds to a time-based profile of values recordable during the simulated execution of the production process;

performing a target determination step comprising:
selecting a recipe template pertinent to the production process out of the plurality of recipe templates;
providing an input value for the at least one variable parameter in the selected recipe template;
simulating the execution of the production process at the target scale using the target setup specification, the selected recipe template, the input value for the at least one variable parameter and the parameter evolution information;
determining, from the simulation, one or more target trajectories for the process parameters;
comparing the source trajectory(ies) and the target trajectory(ies);
computing, based on the comparison and on the at least one acceptability function, an acceptability score for the selected recipe template;
computing an optimal value for the at least one variable parameter in the selected recipe template by optimising the acceptability score and/or computing an acceptable range for the at least one variable parameter, wherein values within the acceptable range yield an acceptability score above a specific threshold;
if there is at least another pertinent recipe template, repeating the target determination step for at least another pertinent recipe template;
selecting at least one of the plurality of recipe templates and corresponding computed value(s) for variable parameter(s) as target recipe based on the acceptability scores computed for one or more recipe templates;
providing the target recipe to a target control system; and
executing, by the target control system, the production process at the target scale based on the target recipe.

2. The computer-implemented method of claim 1, further comprising outputting the target recipe.

3. The computer-implemented method of claim 1, further comprising:
evaluating the performance of the production process at the target scale; and
modifying the at least one acceptability function based on the evaluation.

4. The computer-implemented method of claim 1, wherein a plurality of acceptability functions is received and a plurality of target trajectories are computed, and wherein computing the acceptability score comprises:
for each target trajectory of the plurality of target trajectories obtaining a second partial acceptability score by:
selecting one or more applicable acceptability functions;
for each applicable acceptability function performing a calculation step of:
calculating an acceptability value based on the acceptability function for each time point in the target trajectories;
aggregating the acceptability values at the different time points to obtain a first partial acceptability score;
if there is a single applicable acceptability function, setting the second partial acceptability score to the first partial acceptability score;
if there is a plurality of applicable acceptability functions, aggregating the first partial acceptability scores for all applicable acceptability functions to obtain the second partial acceptability score;
and aggregating the second partial acceptability scores for all target trajectories to obtain the acceptability score.

5. The computer-implemented method of claim 1, further comprising:
defining an aim quantity characterizing the production process at the source scale;
executing, by a source control system, the production process multiple times at the source scale while varying the process parameters and/or the process steps;
selecting, for defining the source recipe, a process based on the result for the aim quantity given by the process parameters and the process steps.

6. A non-transitory computer readable medium comprising computer-readable instructions, which, when loaded and executed on a computer system, cause the computer system to perform operations according to the method of claim 1.

7. A computer-implemented method of scaling a production process to produce a chemical, pharmaceutical and/or biotechnological product, the scaling being from a source scale to an intermediate target scale to a final target scale, wherein the production process is defined by a plurality of steps specified by one or more process parameters controlling an execution of the production process, the method comprising:
retrieving:
parameter evolution information that describes the time evolution of the process parameter(s);
a plurality of recipe templates, wherein:
a recipe comprises the plurality of steps defining the production process, and
a recipe template is a recipe in which at least one of the process parameters specifying the plurality of steps is a parameter being variable and having no predetermined value at the outset;
receiving:
a source setup specification of a source setup to be used for executing the production process at the source scale, the source setup specification comprising the source scale value;
an intermediate target setup specification of an intermediate target setup to be used for executing the production process at the intermediate target scale, the intermediate target setup specification comprising the intermediate target scale value;
a final target setup specification of a final target setup to be used for executing the production process at the final target scale, the final target setup specification comprising the final target scale value;
a source recipe defining the production process at the source scale;
at least one acceptability function defining conditions on the values of the process parameter(s) when the values are considered singularly at any one of the source scale, intermediate target scale and final target scale and/or when the values at any one scale are considered in relation to corresponding values at any another one or more scales;
simulating the execution of the production process at the source scale using the source setup specification, the source recipe and the parameter evolution information;
determining, from the simulation, one or more source trajectories for the process parameter(s), wherein a trajectory corresponds to a time-based profile of values recordable during the simulated execution of the production process;
performing a target determination step comprising:
selecting a recipe template pertinent to the production process out of the plurality of recipe templates;
providing a first input value for the at least one variable parameter in the selected recipe template;
providing a second input value for the at least one variable parameter in the selected recipe template;
simulating the execution of the production process at the intermediate target scale using the intermediate target setup specification, the selected recipe template, the first input value for the at least one variable parameter and the parameter evolution information;
determining, from the simulation, one or more intermediate target trajectories for the process parameters;
simulating the execution of the production process at the final target scale using the final target setup specification, the selected recipe template, the second input value for the at least one variable parameter and the parameter evolution information;
determining, from the simulation, one or more final target trajectories for the process parameters;
making a first, a second and a third pairwise comparison between any two of the source trajectory(ies), the intermediate target trajectory(ies) and the final target trajectory(ies), and making a three-wise comparison among the source trajectory(ies), the intermediate target trajectory(ies) and the final target trajectory(ies);
computing an acceptability score based on at least two comparisons and on the at least one acceptability function;
computing a first optimal value and a second optimal value for the at least one variable parameter by optimising the acceptability score and/or computing a first acceptable range and a second acceptable range for the at least one variable parameter, wherein values within the first acceptable range and values within the second acceptable range yield an acceptability score above a specific threshold;
if there is at least another pertinent recipe template, repeating the target determination step for at least another pertinent recipe template;
selecting at least one of the plurality of recipe templates and corresponding computed value(s) for variable parameter(s) as target recipe based on the acceptability scores computed for one or more recipe templates;
providing the target recipe to a target control system; and
executing, by the target control system, the production process at the target scale based on the target recipe.

8. A computer system operable to scale a production process to produce a chemical, pharmaceutical and/or biotechnological product from a source scale to a target scale, wherein the production process is defined by a plurality of steps specified by one or more process parameters controlling an execution of the production process, the computer system comprising:
a retrieving module configured to retrieve:
parameter evolution information that describes the time evolution of the process parameter(s);
a plurality of recipe templates, wherein:
a recipe comprises the plurality of steps defining the production process, and
a recipe template is a recipe in which at least one of the process parameters specifying the plurality of steps is a parameter being variable and having no predetermined value at the outset;
a receiving module configured to receive:
a source setup specification of a source setup to be used for executing the production process at the source scale, the source setup specification comprising the source scale value;
a target setup specification of a target setup to be used for executing the production process at the target scale, the target setup specification comprising the target scale value;
a source recipe defining the production process at the source scale;
at least one acceptability function defining conditions for the values of the process parameter(s) at the source scale and/or at the target scale; and
a computing module configured to:
simulate the execution of the production process at the source scale using the source setup specification, the source recipe and the parameter evolution information;
determine, from the simulation, one or more source trajectories for the process parameter(s), wherein a trajectory corresponds to a time-based profile of values recordable during the simulated execution of the production process;
perform a target determination step comprising:
selecting a recipe template pertinent to the production process out of the plurality of recipe templates;
providing an input value for the at least one variable parameter in the selected recipe template;
simulating the execution of the production process at the target scale using the target setup specification, the selected recipe template, the input value for the at least one variable parameter and the parameter evolution information;
determining, from the simulation, one or more target trajectories for the process parameters;
comparing the source trajectory(ies) and the target trajectory(ies);
computing, based on the comparison and on the at least one acceptability function, an acceptability score for the selected recipe template;
computing an optimal value for the at least one variable parameter in the selected recipe template by optimising the acceptability score and/or computing an acceptable range for the at least one variable parameter, wherein values within the acceptable range yield an acceptability score above a specific threshold;
if there is at least another pertinent recipe template, repeat the target determination step for at least another pertinent recipe template; and
select at least one of the plurality of recipe templates and corresponding computed value(s) for variable parameter(s) as target recipe based on the acceptability scores computed for one or more recipe templates, wherein the computer system is further configured to be interfaced with a target control system for controlling a target process equipment, wherein the computing module is further configured to provide the target recipe to the target control system, and wherein the target control system is configured to execute the production process at the target scale based on the target recipe.

9. The computer system of claim 8, further comprising an output module configured to output the target recipe.

10. The computer system of claim 8, wherein the computing module is further configured to:
   evaluate the performance of the production process at the target scale; and
   modify the at least one acceptability function based on the evaluation.

11. The computer system of claim 8, further configured to be interfaced with a source control system for controlling a source process equipment, wherein:
   the source control system is configured to execute the production process multiple times at the source scale while varying the process parameters and/or the process steps; and
   the computing module is configured to define an aim quantity characterizing the process at the source scale and to select, for defining the source recipe, a process based on the result for the aim quantity given by the process parameters and the process steps.

* * * * *